United States Patent [19]

Kanand et al.

[11] Patent Number: 5,705,707
[45] Date of Patent: Jan. 6, 1998

[54] PREPARATION OF N-BUTYRALDEHYDE AND/OR N-BUTANOL

[75] Inventors: Jürgen Kanand, Bad Dürkheim; Michael Röper, Wachenheim; Rolf Pinkos; Rocco Paciello, both of Bad Dürkheim; Alfred Thome, Speyer, all of Germany

[73] Assignee: BASF Aktiengesellschaft, Ludwigshafen, Germany

[21] Appl. No.: 676,185

[22] PCT Filed: Jan. 12, 1995

[86] PCT No.: PCT/EP94/00114

§ 371 Date: Jul. 12, 1996

§ 102(e) Date: Jul. 12, 1996

[87] PCT Pub. No.: WO95/19334

PCT Pub. Date: Jul. 20, 1995

[30] Foreign Application Priority Data

Jan. 14, 1994 [DE] Germany ............ 44 00 837.6

[51] Int. Cl.$^6$ ................................ C07C 47/52
[52] U.S. Cl. ............ 568/487; 568/449; 568/450; 568/904
[58] Field of Search ................ 568/449, 450, 568/487, 904

[56] References Cited

U.S. PATENT DOCUMENTS

| 2,922,822 | 1/1960 | Beach et al. ............ 260/614 |
| 4,310,709 | 1/1982 | Rebafka et al. ............ 568/687 |

FOREIGN PATENT DOCUMENTS

| 2550902 | 5/1977 | Germany. |
| 9103449 | 3/1991 | WIPO. |

*Primary Examiner*—C. Warren Ivy
*Assistant Examiner*—Sreeni Padmanabhan
*Attorney, Agent, or Firm*—Keil & Weinkauf

[57] ABSTRACT

A process for the preparation of n-butyraldehyde and/or n-butanol, wherein a) 1,3-butadiene is caused to react with an alcohol of the formula I

ROH        I, to form a mixture of adducts of the formulas II

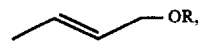

II and III

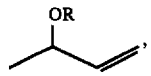

III b) the adduct III is isomerized to the adduct II,
c) the adduct II is isomerized in the presence of a homogeneous or heterogeneous transition metal element catalyst to form the enol ether of the formula IV

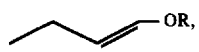

IV and d) n-butyraldehyde and/or n-butanol is/are produced from this ether IV by the reaction thereof with hydrogen and water or water only in the presence of a homogeneous or heterogeneous catalyst.

41 Claims, 1 Drawing Sheet

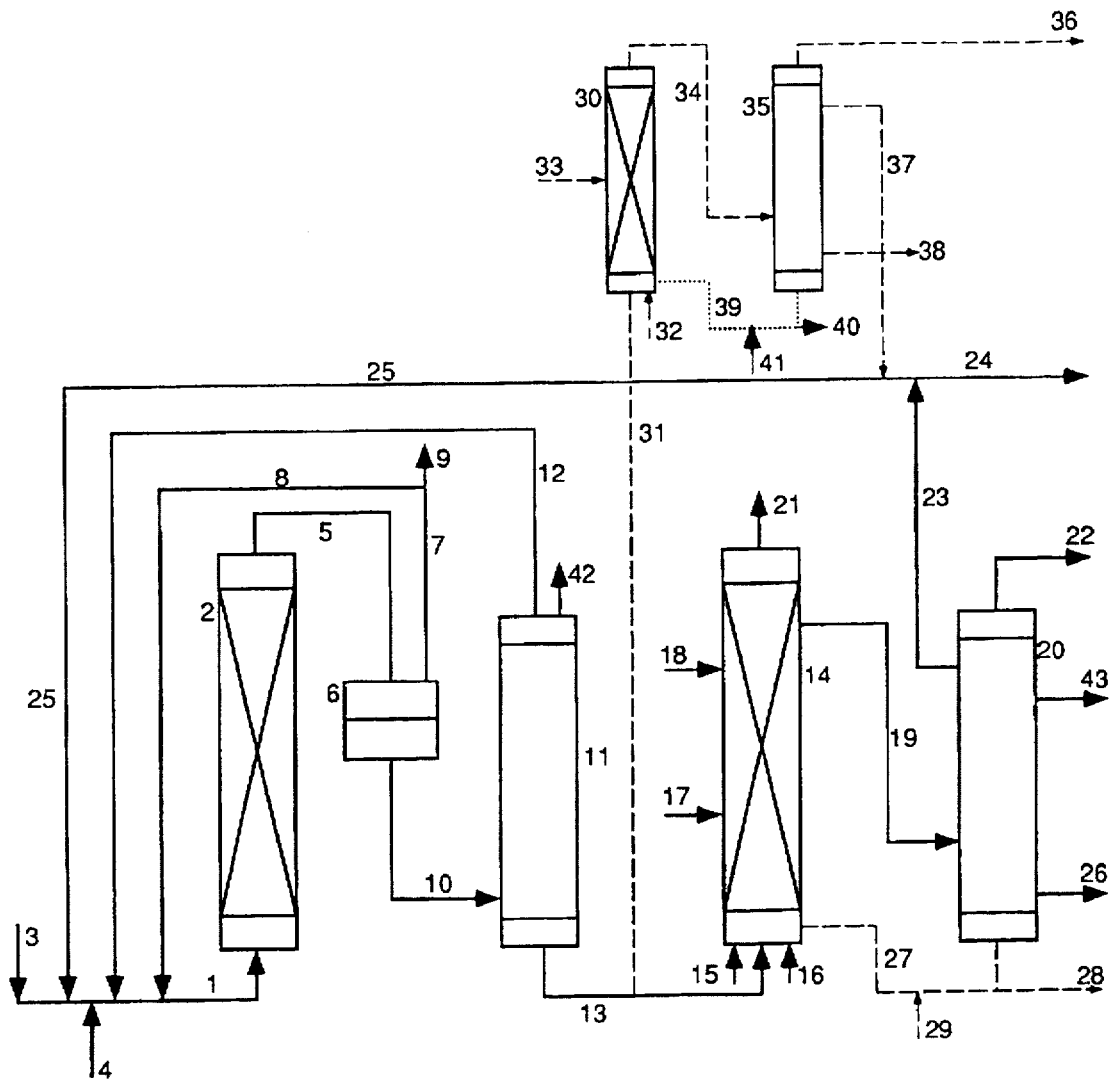

PREPARATION OF N-BUTYRALDEHYDE AND/OR N-BUTANOL

This is the U.S. National Stage Application of PCT/EP94/0014 filed Jan. 12, 1995 now WO 95/19334 published Jul. 20, 1995.

The present invention relates to a process for the preparation of n-butyraldehyde and/or n-butanol.

n-Butyraldehyde and n-butanol are products which are produced on a large scale in the chemical industry and have varied uses. n-butyraldehyde, for example, is produced world-wide in amounts of more than 4 million t/yr and serves inner alia as starting material for the preparation of plasticizer alcohols. n-butanol is employed on a large scale as solvent, for example for coating compositions.

n-Butyraldehyde is prepared nowadays on an industrial scale virtually exclusively by the hydroformylation of propene, for which purpose various processes are used, which essentially make use of cobalt or rhodium hydroformylation catalysts, (Kirk-Othmer: Encyclopedia of Chemical Technology, 4th Edition, Vol. 4, pp. 741–746, John Wiley Sons, New York 1992).

n-Butanol is one of the quantitatively most important derivatives of n-butyraldehyde and is obtained therefrom by hydrogenation. Other processes for the preparation of n-butanol, such as the hydrogenation of crotonaldehyde, which is in turn produced by aldol condensation of acetaldehyde, are nowadays merely of historical interest or have only regional significance, such as in the case of the microbiological production of n-butanol by fermention of molasses, (Kirk-Othmer: Encyclopedia of Chemical Technology, 4th Edition, Vol. 4. pp. 694–696: John Wiley Sons, New York 1992). These processes, particularly the hydroformylation of propene, demand high investments, for example, for the construction of high-pressure plant for the cobalt-catalyzed hydroformylation or for the purchase of the expensive rhodium catalyst, the plant required for handling during hydroformylation and for working up the spent rhodium-containing catalyst solution. Furthermore the preparation of n-butyraldehyde by the hydroformylation process requires the presence of a synthesis gas plant for the preparation of the synthesis gas required for the hydroformylation. A further drawback of the process is the unavoidable formation of large quantities of the by-product isobutyraldehyde, which, on account of its restricted possibility of further usage in quantity, has a low economic rating.

1,3-Butadiene is a basic chemical which is produced in large amounts in steam crackers and is isolated, by extraction, from the $C_4$ cut obtained in the cracker, for example, by means of N-methyl pyrrolidone. Although 1,3-butadiene is available in large amounts and is a very cheap raw material, no industrially usable process has been developed hitherto for the preparation of n-butyraldehyde or n-butanol on the basis of 1,3-butadiene. One reason for this is the tendency of 1,3-butadiene to undergo dimerization and polymerization reactions and the formation of mixtures of 1,2- and 1,4-adducts in addition reactions. The reason for this chemical behavior is the presence of two conjugated double bonds in the 1,3-butadiene molecule (Kirk-Othmer: Encyclopedia of Chemical Technology, 4th Edition, Vol. 4. pp. 676–683, John Wiley & Sons, New York 1992).

U.S. Pat. No. 2,922,822 and DE-A 2,550,902 disclose that alcohols react in the liquid phase with 1,3-butadiene in the presence of acid ion exchangers to form the corresponding unsaturated ethers. U.S. Pat. No. 2,922,822 carries out this reaction in the presence of a large excess of methanol, which leads to an increased formation of the undesirable dimethyl ether. According to the process described in DE-A 2,550,902 vinyl cyclohexene forms during this reaction as main product. In EP-A 25,240 the addition of alcohol to 1,3-butadiene is advantageously carried out in the presence of a polar, aprotic solvent, which must then again be removed, by distillation. In GB-A 943,160 the addition of alcohols is carried out by means of Brönsted acids in the presence of copper salts.

Transition metal complexes with phosphine ligands have also been used as catalysts for the addition of alcohols to 1,3-butadiene. Chauvin et al (Bull. Chim. Soc. France 652 (1974)) examined the addition of alcohol to 1,3-butadiene using trialkyl and triaryl phosphine complexes of nickel and palladium. In some cases alcoholates, particularly phenolates, have been employed as co-catalysts for this reaction. In DD-A 206,989 alkylpalladium(II) complexes with trialkyl or triaryl phosphine or phosphite ligands are used for the reaction of isoprene with alcohol in the presence of alkali metal alcoholates. Kawazura et al(J. Chem. Soc. Chem. Com. 2213, (1972)) use rhodium(III) chloride as catalyst, also Dewhirst (J. Org Chem 32, 1297 (1967)). Taylor (Symposium on New Routes to New Olefins; Division of Petroleum Chemistry, Inc.; American Chemical Society, Boston Meeting, 1972) examined the addition of alcohol to 1,3-butadiene using copper(I) chloride and rhodium(I)/alkadiene complexes. Jolly et al (Synthesis 771 (1990)) mention the reaction of 1,3-butadiene with trialkyl phosphine/palladium complexes. In all of the reactions cited mixtures of 3-alkoxybutene-1 and 1-alkoxybutene-2 are formed. In many of these reactions of the prior art the conversion and yield are unsatisfactory and a large number of oligomeric butadiene derivatives are formed, for which there is virtually no use or which can be used only in such small amounts that the major portion of these by-products unavoidably formed in a large-scale process would have to be discarded as waste.

For the isomerization of allyl ethers to enol ethers a series of reagents has already been examined. According to Baudry et al (J. Chem. Soc. Chem. Comm. 694(1978)) 1-methoxybutene-1 forms in the reaction of 1-methoxybutene-2 in the presence of a cationic iridium complex. Tatsumi et al (J. Organomet Chem 252, 105 (1983)) use a molybdenum complex for this reaction. According to Menicagli et al (J. Org Chem 52, 5700 (1987)) a ruthenium/triphenyl phosphine/hydride complex is used for the isomerization of acetalic ether to form acetalic vinyl ether. Suzuki et al (Tetrahedron Lett. 21, 4927 (1980)) use similar ruthenium complexes for the isomerization of cyclic allyl ether acetals to the corresponding vinyl ether acetals.

In addition to the aforementioned homogeneous catalysts heterogeneous catalysts have also been employed for the isomerization of ethers to enol ethers in the liquid phase. The chemical rearrangement of allylphenyl and alkyl ethers in the presence of palladium on activated charcoal catalysts leads, according to Boss et al (Angew. Chem 88, 578 (1976)), to the corresponding enol ether, from the methylvinyl grouping of which propionaldehyde is then liberated in the presence of water and acid. WO 91/03449 relates to a process for the isomerization of allyl ethers to enol ethers by means of supported ruthenium or rhodium catalysts under anhydrous conditions.

The direct single-stage conversion of allyl ethers to the corresponding saturated alcohols is not known.

It was thus the object of the present invention to provide an economical process which can be employed on an industrial scale for the preparation of n-butyraldehyde and/or n-butanol, which makes it possible to prepare these products at high yield and selectivity. In particular, the amount of by-product formed in the process should be low or the said by-products should themselves be sought-after commercial products. Furthermore the process should be flexible so as to make it possible to prepare n-butyraldehyde and/or n-butanol as required, in accordance with the demand for these compounds. The process should not demand the presence of a synthesis gas plant or necessitate the use of high pressure facilities.

Accordingly, we have found a process for the preparation of n-butyraldehyde and/or n-butanol, wherein a) 1,3-butadiene is caused to react with an alcohol of the formula I $$\text{ROH} \qquad \qquad \text{I}$$

in which the radical R is a $C_2$–$C_{20}$ alkyl or alkenyl group which may be unsubstituted or substituted by 1 or 2 $C_1$–$C_{20}$ alkoxy or hydroxy groups, or R is a $C_6$–$C_{10}$ aryl group or a $C_7$–$C_{11}$ aralkyl group or the methyl group, at elevated temperature and under superatmospheric pressure in the presence of a Brönsted acid or in the presence of a complex of a Group Ib, VIIb, or VIIIb element with ligands containing phosphorus or nitrogen to form a mixture of the adducts of the formulas II

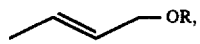

and III

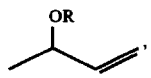

b) the adduct III is isomerized to the adduct II,
c) the adduct II is isomerized in the presence of a homogeneous or heterogeneous transition metal element catalyst in the liquid phase or in the presence of a heterogeneous catalyst containing a transition metal element in the gaseous phase to form the enol ether of the formula IV

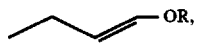

and d) n-butyraldehyde and/or n-butanol is/are produced from this ether IV by the reaction thereof with hydrogen and water or water only in the presence of a homogeneous or heterogeneous transition metal element catalyst in the liquid phase or in the presence of a transition metal element containing heterogeneous catalysts in the gaseous phase and the alcohol ROH I is again liberated, and the liberated alcohol ROH I is recycled to the stage defined as partial reaction a).

The process of the invention is thus composed of four partial reactions a) to d). The reactions c) and d) can be carried out individually, successively, in at least 2 process stages or virtually simultaneously in a single process stage, as required. The same applies to the reactions a) and b), in which case the isomerization of the adduct III to the adduct II in accordance with partial reaction b) takes place following recycling of the adduct III to the process stage involving the addition of the alcohol ROH to 1,3-butadiene concurrently with the addition reaction defined as partial reaction a). By this means it is a simple matter to adjust the process parameters for the process of the invention to the local conditions at the site where a plant for carrying out the process is installed, for example by integrating plant units already present at the site in the system required for the process of the invention. Furthermore the process of the invention can be designed in such a way that no expensive nobel metal catalysts need be used, if such is desired.

The term "process stage" is used in this application for a plant unit, in which any one of the reactions a) to d) takes place over the catalyst(s) employed in this plant unit or in which a number, particularly two, of these reactions, occur in parallel over the catalyst(s) used in this plant unit. The hydrolysis or the combined hydrolysis/hydrogenation of the enol ether IV defined as partial reaction d) is, unless otherwise stated in this application, considered to be an individual partial reaction.

If the catalyst used in a plant unit or if each the catalysts used in a plant unit is capable of catalyzing, under the reaction conditions used therein, for example, the isomerization of the adduct II to the enol ether IV defined as partial reaction c) and the hydrolysis or hydrogenation of the enol ether IV to n-butyraldehyde and/or n-butanol defined as partial reaction d), so that no strict spatial separation of these reactions in the unit can be ascertained, this application speaks of the execution of the reactions c) and d) as being in a 'single process stage'. A unit can include both a single reactor and a number of in-line reactors, which are filled with the same or, optionally, different catalysts and are operated in the same mode of operation and under the same or different temperature and pressure conditions. By 'mode of operation' we mean operating either in the liquid phase using a homogeneous catalyst or operating in the liquid phase using a heterogeneous catalyst or operating in the gaseous phase. It follows then that this application will not speak of, for example, a 'reaction in a single process stage', if in the individual successive reactors catalysts are used, which are capable only of catalyzing one specific reaction or if these reactors are operated with different operational modi.

The process of the invention is described in greater detail below:

In the process stage a) 1,3-butadiene is caused to react with the alcohol ROH I in the presence of a catalyst according to equation (1)

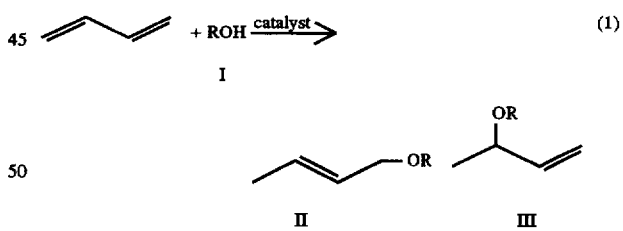

to form the 1,4-adduct of formula II and the 1,2-adduct of formula III. In the resulting 1,4-adduct II the double bond can be present in both the cis and trans forms, but this bears no relevance on the further course of the process. The adducts II and III are formed, depending on the reaction conditions and catalyst used, generally in a molar ratio of from 1:1 to 1:3.

The nature of the alcohol ROH I employed in the reaction is not usually crucial for the process. Both primary and secondary alcohols can be used, although primary alcohols are preferably employed. It is possible to use aliphatic, cycloaliphatic, aromatic, and araliphatic alcohols, but aliphatic and araliphatic alcohols are preferably employed. Generally alcohols ROH I are used in the process of the invention in which the radical R, can be a $C_1$–$C_{20}$ alkyl group, a $C_2$–$C_{10}$ alkenyl group, eg, the but-2-enyl group, preferably a $C_1$–$C_4$ alkyl group, particularly the n-butyl group, a $C_6$–$C_{10}$ aryl group, preferably the phenyl group, or a $C_7$–$C_{11}$ aralkyl group, preferably the benzyl group. The radicals R, can be optionally substituted by substituents such as $C_6$–$C_{10}$ alkoxy and/or hydroxyl groups. The alcohols ROH I used can thus be diols or triols or alkoxy alcohols. Since these substituents usually have no critical influence on the reaction, alcohols ROH I are preferably used which have unsubstituted radicals R. Of course alcohols having a higher number of carbon atoms can be used, if desired. Since such higher alcohols are usually more expensive than lower alcohols, lower alcohols are preferably used for economical reasons.

A large number of catalysts can be used in process stage a), for example, Brönsted acids or alternatively phosphine complexes of Group Ib, VIIb, or VIIIb transition metals, particularly complexes of palladium and nickel.

The Brönsted acids used can be, for example, conventional, non-oxidizing Brönsted acids, such as hydrohalic acids, eg, hydrochloric acid, sulfuric acid, phosphoric acid, perchloric acid, hydrofluoric acid, tetrafluoroboric acid, methanesulfonic acid, or toluenesulfonic acid. However solid Brönsted acids, particularly organic or inorganic cation exchangers, are preferably employed.

By organic cation exchangers we mean pulverulent, gellike, or macroporous, polymeric polyelektrolytes, which carry Brönsted acidic functional groups, such as sulfonic or phosphonic acid groups or carboxyl groups, on a polymeric matrix, for example, sulfonated phenol-formaldehyde resins, sulfonated poly(styrene-CO-divinyl benzene)s, sulfonated polystyrene, poly(perfluoroalkylenesulfonic acid)s, or sulfonated coals. In the process of the invention these cation exchangers can be used in the form of commercial products such as are available under the trade names Amberlite®, Dowex®, Amberlyst®, Lewatit®, Wofatit®, Permutit®, and Nation®. Advantageously, the exchangers are used in the process of the invention in their protonized form, the so-called $H^+$ form. Suitable organic cation exchangers are, for example, the commercial products Amberlite® 200, Amberlite® IR 120, Amberlite® IR 132 E, Lewatit® SC 102, Lewatit® SC 104, Lewatit® SC 108, Lewatit® SPC 108, Lewatit® SPC 112, Lewatit® SPC 118 and Amberlyst® 15.

Further advantageous results can be obtained in the process of the invention by using modified organic cation exchangers, for example, those which additionally contain Lewis acids, such as copper(II) halides, particularly copper (II) chloride, copper(II) bromide, copper(II) iodide, or copper(II) salts, such as copper(II) sulfate, copper(II) nitrate, or copper(II) acetate. Such Lewis acid-containing cationic ion exchangers can be prepared, eg, by the process described in GB-A 943,160. Preferably the above Lewis acid-containing ion exchangers are employed in a form in which only some of the hydrogen ions of the acidic groups of the ion exchanger are substituted by the Lewis acid cation, while the remaining acidic groups continue to function as Brönsted acids. Generally the organic ion exchangers are doped with an amount of Lewis acid such that from 5 to 15 mol %, preferably from 10 to 40 mol %, in particular from 15 to 30 mol % of the ions of the acidic groups present on the ion exchanger are substituted by the respective Lewis acid.

Instead of organic, acidic cation exchangers use can be made in the process of the invention of solid, Brönsted acid-like inorganic solids, for example, zeolites, such as β-zeolites or Y-type zeolites in the $H^+$ form, fuller's earths, such as bentonites, montmorillonites, or attapulgites, nonzeolitic molecular sieves based on phosphate such as are dealt with in U.S. Pat. No. 4,440,871, U.S. Pat. No. 4,310,440, U.S. Pat. No. 4,567,029, U.S. Pat. No. 4,554,143, U.S. Pat. No. 4 4,500,651, EP-A 158,976, EP-A 158,349, EP-A 159,624, as well as acidic or acid-impregnated metal oxides, the preparation of which is described, eg in U.S. Pat. No. 4,873,017. Preferred acidic inorganic solids are β-zeolites or Y-type zeolites in the $H^+$ form, particularly β-zeolites in the $H^+$ form. βzeolites can be obtained eg, by the process defined in U.S. Pat. No. 4,891,458.

Preferably organic ion exchangers are used in the process of the invention for the addition of alcohols ROH I to 1,3-butadiene in partial reaction a).

If in partial reaction a) of the process of the invention liquid or dissolved Brönsted acid catalysts, particularly sulfuric acid, phosphoric acid, toluenesulfonic acid, methanesulfonic acid or tetrafluoroboric acid are employed, the reaction is generally carried out by introducing the alcohol ROH and 1,3-butadiene in liquid or preferably gaseous form into the acid used as initial substance and the resulting adducts of the formulas II and III are removed from the reaction zone, by distillation or stripping. This can be achieved by using conventional reactors such as bubble-cap columns, loop reactors, and the like. Advantageously the alcohol/1,3-butadiene mixture can be introduced into the acid, eg, by means of jet nozzles. The adducts II and III can be separated from the aqueous solution of the Brönsted acid by means of phase separators. Instead of bubble-cap columns or loop reactors it is possible to use cascades of stirred boilers, while advantageously operating under a pressure at which the 1,3-butadiene is liquid under the reaction conditions used.

However, it is preferred to use solid Brönsted acids in the process according to the invention in the form of the aforementioned organic or inorganic catalysts, in particular in the form of organic ion exchangers. These are preferably used in the form of a fixed bed through which the liquid reaction mixture flows in an upward or downward direction. The fixed catalyst bed can be installed, eg, in tubular reactors or preferably in cascades of reactors. Another possibility is to pass the reactants as a gas through the catalyst bed, but it is preferred to operate in the liquid phase. Of course, the addition of the alcohol ROH to 1,3-butadiene defined as partial reaction a) can be carried out continuously or batchwise. The molar ratio of alcohol to 1,3-butadiene used in the process according to the invention can be in a wide range. Generally a molar ratio of alcohol ROH to 1,3-butadiene of from 0.5:1 to 5:1, preferably from 1:1 to 2.5:1 and particularly from 1.5:1 to 2.5:1 is preferably used. When carrying out the process in the liquid phase, the reaction of the alcohol ROH with 1,3-butadiene is generally caused to take place at temperatures of from 20° to 150° C., preferably from 50° to 120° C., particularly from 70° to 110° C. and under a pressure of generally from 10 to 100 bar, preferably from 10 to 50 bar, particularly from 20 to 30 bar. Advantageously the pressure used is such that the 1,3-butadiene is liquid at the reaction temperature used. The use of a higher pressure is possible. The optimum temperature of reaction to be used with regard to the Brönsted acid catalyst employed is advantageously determined in each case in a preliminary test. If mineral acids or strongly acidic ion exchangers, such as Nation®, are used as catalysts, the reaction takes place without heating. Generally the alcohol ROH/1,3-butadiene mixture is passed through the fixed catalyst bed at a space velocity of from 0.01 to 0.5 $g/cm^3$.h, preferably from 0.02 to 0.4 g/cm³.h and more preferably from 0.02 to 0.05 g/cm³.h. The addition of a solvent to the reaction mixture is possible but not generally necessary, since the alcohol employed and the adducts II and III can also function as solvents. The residence time of the alcohol ROH/1,3-butadiene mixture in the reactor is generally from 1 to 6 h and is usually governed by the temperature of reaction used.

If the addition of the alcohol ROH to 1,3-butadiene is carried out in the gaseous phase, temperatures are generally used which are below 120° C., the pressure generally being less than 20 bar. The reaction gas can be mixed, if desired, with a gas inert under the reaction conditions, eg, nitrogen, but generally the reaction gas is used undiluted.

In another embodiment of the process of the invention the addition of the alcohol ROH I can effected by means of a catalyst homogeneously dissolved in the reaction medium or a heterogenized catalyst, which catalyst contains a Group Ib, VIIb, or VIIIb element such as copper, nickel, rhodium, palladium, platinum, rhenium, or iridium, preferably palladium or nickel.

Advantageously these transition metal element catalysts, particularly the palladium and nickel catalysts, are employed in the form of complexes which are homogeneously soluble in the reaction medium, eg, their complexes with a phosphine, 2,2-bipyridine, or 1,10-phenanthroline ligand. In the process of the invention a large number of different phosphine, 2,2-bipyridine, or 1,10-phenanthroline ligands can be used for this purpose for complexing the Group VIIb, or VIIIb metals, particularly palladium and nickel. Suitable ligands are both monodentate and polydentate, particularly bidentate, phosphine ligands. Suitable ligands are, eg, trialkyl phosphines, triaryl phosphines, alkyldiaryl phosphines, aryldialkyl phosphines, aryl diphosphines, alkyl diphosphines, and arylalkyl diphosphines. The alkyl group-carrying ligands may contain the same or different $C_1$–$C_{10}$, preferably $C_1$–$C_6$, alkyl or cycloalkyl groups. The aryl group-carrying ligands can contain the same or different $C_6$–$C_{12}$ aryl groups, particularly the phenyl or naphthyl group, or alternatively diphenyl groups. Furthermore ligands for complexing the Group Ib, VIIb, or VIIIb elements can be used which carry heterocycloaliphatic groups such as pyrrolidine, imidazolidine, piperidine, morpholine, oxazolidine, piperazine, or triazolidine groups or heteroaromatic groups such as pyrrole, imidazole, oxazole, indole, pyridine, quinoline, pyrimidine, pyrazole, pyrazine, pyridazine, or quinoxaline groups together with other alkyl or aryl groups. The alkyl or aryl groups of the ligands can be unsubstituted or carry substituents which are inert under the reaction conditions, such as $C_1$–$C_4$ alkoxy or di($C_1$–$C_4$ alkyl)amino, $C_1$–$C_6$ alkyl, nitro, cyano or sulfonate groups.

Theoretically there is no limit to the usability of such ligands for complexing the Group Ib, VIIb, or VIIIb elements, particularly palladium and nickel, in the process of the invention. However for reasons of cost it is preferred to use ligands which can be prepared in a simple manner.

A list of such ligands is given below merely by way of example: trimethylphosphine, triethylphosphine, tripropylphosphine, triisopropylphosphine, tributylphosphine, trioctylphosphine, tridecylphosphine, tricyclopentylphosphine, tricyclohexylphosphine, triphenylphosphine, tritolylphosphine, cyclohexyldiphenylphosphine, tetraphenyldiphosphinomethane, 1,2-bis(diphenylphosphino)ethane, tetramethyldiphosphinomethane, tetraethyldiphosphinomethane, 1,3-bis(diphenylphosphino)propane, 1,4-bis(diphenylphosphino)butane, tetra-t-butyldiphosphinomethane, 1,2-bis(dimethylphosphino)ethane, 1,2-bis(diethylphosphine)ethane, 1,2-bis(dipropylphosphino)ethane, 1,2-bis(diisopropylphosphino)ethane, 1,2-bis(dibutylphosphino)ethane, 1,2-bis(di-t-butylphosphino)ethane, 1,2-bis(dicyclohexylphosphino)ethane, as well as the bisphosphine ligands described in EP-A 279,018, EP-A 311,619, WO 90/06810 and EP-A 71,281. Apart from using the processes described in the aforementioned patent applications, the alkyl or aryl phosphine ligands can be prepared by conventional methods as described, for example, in Houben-Weyl, Methoden der Organischen Chemie, Vol. XII/1, 4th Edition, pp. 17–65 and pp. 182–186, Thieme, Stuttgart, 1963 and Vol. E 1, 4th Edition, pp. 106–199, Thieme, Stuttgart, 1982.

In addition to phosphine ligands use can be made in the process of the invention, to advantage, of 2,2-bipyridine or 1,10-phenanthroline ligands of alkyl- or aryl-substituted or anellated 2,2-bipyridine or 1,10-phenanthroline derivatives, which contain the (—N=C—C=N—) grouping responsible for the complexing property of the 2,2-bipyridine or 1,10-phenanthroline ligands, for example, 2,2-biquinoline, 4,7-diphenyl-1,10-phenanthroline, 2,9-dimethyl-4,7-diphenyl-1,10-phenathroline, 4,5-diazafluorene, dipyrido[3,2-a:2',3'-c]phenazine, 2,2',6',2"-terpyridine and the like,. Some of these ligands are commercially available, eg, 2,2-bipyridine or 1,10-phenanthroline, or can be prepared by the methods described in Synthesis 1, (1976) or Aust. J. Chem. 23, 1023 (1970).

The complexes of Group Ib, VIIb, or VIIIb elements, particularly of palladium and nickel, which can be used in the process of the invention for the partial reaction a) can be produced in situ in the reaction mixture or be preformed and added to the reaction mixture. For the formation in situ of these complexes it is general to operate in such a manner that compounds of the Group Ib, VIIb, or VIIIb elements, eg, their halides, preferably their chlorides, bromides, or iodides, the nitrates, cyanides or sulfates, or complex compounds of these metals, such as acetylacetonates, carboxylates, carbonyl complexes or olefin complexes, such as ethene or butadiene complexes, are fed in to the reaction mixture together with the respective ligands, after which the complexes that can be used in the invention in partial reaction a) are formed in the reaction mixture. In this method the complexing agent is generally added in a molar ratio with respect to the Group Ib VIIb, or VIIIb element of from 2:1 to 200:1, preferably from 2:1 to 10:1, and more preferably from 2:1 to 4:1.

Generally, when effecting the addition of the alcohol ROH to 1,3-butadiene in process stage a) of the process of the invention, when use is made of the said Group Ib, VIIb, or VIIIb element complex catalysts, particularly the palladium complex catalysts, a molar ratio of 1,3-butadiene to Group Ib, VIIb, or VIIIb element of from 100:1 to 100,000:1, preferably of from 200:1 to 2000:1 and more preferably of from 400:1 to 1000:1 is used, and when the process is carried out continuously this molar ratio is based on the steady 1,3-butadiene concentration in the liquid reaction mixture.

The molar ratio of alcohol ROH to 1,3-butadiene can, in this embodiment of the process, be chosen within wide limits and is usually not critical. For example, the alcohol to be added to 1,3-butadiene can function not only as a reagent but also as a solvent for the complex catalyst. Generally therefore the process of the invention uses in the partial reaction a) a molar ratio of alcohol to 1,3-butadiene of from 0:1 to 10:1, preferably from 1:1 to 5:1 and more preferably from 1:1 to 2:1, whilst in the case of the continuous embodiment of the process these figures relate to the steady 1,3-concentration in the liquid reaction mixture.

The addition of the alcohol ROH to 1,3-butadiene defined as partial reaction a) of the process of the invention with the aid of the complex catalysts mentioned above is preferably carried out in the liquid phase. Generally the catalyst is dissolved in the liquid reaction medium used as initial substance and 1,3-butadiene is introduced into the reaction mixture in liquid or gaseous form, together with the alcohol. The reaction medium used can be the alcohol to be added to 1,3-butadiene or a solvent that is inert under the reaction conditions, preferably a high-boiling solvent. Examples of suitable solvents are condensation products which are formed during the reaction, such as alkoxy octadienes, alkoxy dodecatrienes, and also ethers, such as dibutyl ether, diethylene glycol dibutyl ether, low molecular weight poly(ethylene glycol ether)s as well as sulfones, such as sulfolane.

When the process is carried out batchwise, the reaction is generally carried out in a stirred autoclave. The adducts of formulas I and III formed during this process are then advantageously separated from the reaction mixture by distillation, whilst the homogeneous catalyst containing the Group Ib, VIIb, or Group VIIIb element, particularly palladium or nickel, remains at the bottom of the distillation column, dissolved in the high-boiling solvent,. The catalyst solution thus remaining at the base of the distilling apparatus can be re-used for further reactions. When the process is carried out continuously, the 1,3-butadiene is introduced, preferably in liquid form under pressure, into the reaction mixture containing the alcohol ROH and the homogeneously dissolved transition metal element catalyst as well as, optionally, a high-boiling solvent. The reaction is advantageously carried out in a tubular reactor or preferably in a cascade of reactors. Unconverted 1,3-butadiene is advantageously recycled during this process. The alcohol ROH is advantageously continuously metered into the reaction mixture at the rate at which it is consumed in the reaction.

In another continuous embodiment of the process of the invention the 1,3-butadiene can be passed in the gaseous state through the liquid reaction medium containing the catalyst, while unconverted 1,3-butadiene is used to strip the relatively readily volatile adducts of the formulas II and III which are formed with the alcohol during the reaction, from the reaction mixture. The alcohol ROH can be continuously added to the reaction mixture during this process, at a rate corresponding to its rate of consumption during the reaction.

The addition of the alcohol ROH to 1,3-butadiene in the presence of the said complexes of the Group Ib, VIIb, or VIIIb elements, particularly palladium or nickel, is generally carried out at a temperature of from 20° to 180° C., preferably from 50° to 150° C. and more preferably from 80° to 120° C. and under a pressure preferably of from 6 to 10 bar and more preferably under autogenous pressure.

In the process of the invention it is advantageous for the addition of the alcohol ROH to 1,3-butadiene in partial reaction a) to use heterogenized catalysts, preferably those in which the Group Ib, VIIb, or VIIIb element, particularly palladium or nickel, is attached to polymeric matrices. Such polymeric matrices can be resins, such as styrene-divinylbenzene resins or phenol-formaldehyde resins, to which the respective chelate ligands, ie phosphines, 1,10-phenanthrolines or 2,2-bipyridines, are attached, which on the other hand form complexes with the Group Ib, VIIb, or VIIIb elements, particularly palladium or nickel, and thus quasi immobilize them. Suitable heterogeneous matrices for the immobilization of the Group Ib, VIIb or VIIIb element complexes, particularly the palladium and nickel complexes, are inorganic support materials, following previous hydrophobization and chemical modification of their surface by means of organic reagents. Such heterogenized, polymerically attached Group Ib, VIIb, or VIIIb element complexes, particularly palladium and nickel complexes, can be obtained, for example, by the process described in Zhuangyu et al (Reactive Polymers 9, 2499, 2 (1988)). Immobilized complexes of the Group Ib, VIIb, and VIIIb elements can be obtained eg. by the processes described in Hartley, Adv. Organomet. Chem. 15, 189 (1977), F. R. Hartley "Supported Metal Complexes", Riedel, Dordrecht 1985, K. Smith, "Solid Supports and Catalysis in Organic Synthesis", Ellis Horwood, Prentice Hall, N.Y. 1992; C. H. Pittman "Polymer supported Reactions in Organic Synthesis", p. 249, Wiley, Chichester 1980 and C. H. Pittmann. Ann. Chem. Soc. 98, 5407 (1976) as well as Am. N. Y. Acad. Sci. 245, 15 (1977). The advantage of the use of such heterogenized catalysts lies particularly in the greater ease of separation of the catalyst from the reaction products and the more gentle separation achieved. This catalyst can be in the form of a fixed bed through which the reaction mixture flows or it can alternatively be suspended in the reaction mixture and mechanically separated therefrom on completion of the reaction.

Instead of using pure 1,3-butadiene there can be used in the process of the invention 1,3-butadiene-containing hydrocarbon streams as raw material. Such streams are produced, for example, as a so-called $C_4$ cut in steam crackers. Advantageously these streams are, prior to use in the process of the invention, relieved of any acetylenic or allenic hydrocarbons contained therein, by partial hydrogenation (Weissermel, Arpe: Industrielle Organische Chemie; 3rd Edition, VCH Verlagsgesellschaft, Weinheim 1988). The 1,3-butadiene-containing streams can then be introduced in a similar manner to the pure 1,3-butadiene into the partial reaction a) of the process of the invention. Advantageously the saturated or monoolefinic hydrocarbons contained in these hydrocarbon streams which have not reacted during the reaction taking place in partial reaction a) are removed from the effluent from partial reaction a), for example by means of a gas/liquid separator. The adducts of formulas II and III obtained in the reaction of these streams in partial reaction a) of the process of the invention can be further processed, as described below, to form n-butyraldehyde and/or n-butanol, in the same manner as the adducts II and III produced with pure 1,3-butadiene in reaction a).

The effluent from partial reaction a) of the process of the invention generally contains, in addition to unconverted 1,3-butadiene, the adducts of formulas II and III as well as, possibly, particularly when using Brönsted acids as catalysts in partial reaction a), a number of isomers of the respective alkoxy octadiene, which are referred to below collectively as alkoxy octadienes. The alkoxy octadiene forms when effecting the addition of the alcohol ROH to 1,3-butadiene in a side reaction, in which initially 1,3-butadiene is dimerized to octatriene followed by addition of the alcohol ROH thereto to form the octadiene. In addition to these constituents, the effluent from partial reaction a) can contain small amounts of other by- products, for example, octatriene, vinylcyclohexene, dodecatrienes, formed by trimerization of the 1,3-butadiene to dodecatetraene followed by addition of the alcohol ROH, and also dodecatetraene, dialkoxy octene and dialkoxybutane. The formation of these by-products can be influenced and if desired minimized by controlling the type of reaction to take place in partial reaction a), for example, by manipulating the 1,3-butadiene-to-alcohol ROH ratio in the reaction mixture, the temperature of reaction, and the pressure.

The adduct required for the preparation of n-butyraldehyde and/or n-butanol in the process of the invention is the 1-alkoxybutene-2 of formula II, which, for the preparation of the target compounds, can be separated in the process of the invention from its isomer 3-alkoxybutene-1 of formula III contained in the effluent in the same order of magnitude. Since, when effecting the addition of the alcohol ROH to 1,3-butadiene, the adducts II and III are formed in approx. the same amounts. The process according to the invention would be uneconomical on an industrial scale, if it were not possible to convert the 3-alkoxybutene-1III in an economical manner to the desired 1-alkoxybutene-2 II. We have now found, surprisingly, that the conversion of the adduct III to the desired adduct II can be accomplished in a simple and economical manner.

For this purpose, the adduct III is initially separated from the isomeric adduct II present in the effluent resulting from the partial reaction a). This can advantageously be effected by passing the effluent from partial reaction a), after previously removing unconverted 1,3-butadiene, eg, in a separator, to a distillation apparatus and causing the desired separation therein by fractional distillation.

This fractional distillation can also be utilized to separate the adduct II from the by-products present in the effluent from partial reaction a), ie, 1,3-butadiene dimers and trimers as well as their adducts with the alcohol ROH and possibly polyalkoxylated by-products. Since these by-products generally have no adverse effect on the rest of the process of the invention, separation thereof can be omitted. Alternatively, the distillation may be operated such that in addition to the adduct III only some of the by-products, particularly the olefinic 1,3-butadiene dimers and trimers as well as polyalkoxylated by-products, are separated; whilst other by-products, particularly the octadienes and if desired the alkoxy dodecatrienes, are processed together with the adduct II in the subsequent reactions, the end products formed from these by-products from the partial reaction a) being octanols or dodecanols, which are desirable plasticizer alcohols.

The separation, by distillation, of the readily volatile adduct III from the adduct II can be carried out in a simple manner, eg, in conventional distillation columns. The adduct III separated from the desired adduct can, as also the unconverted 1,3-butadiene, then be recycled to the partial reaction process stage a) of the process of the invention. Recycling of the adduct III to the process stage defined as the partial reaction a) of the process of the invention causes the isomerization of the adduct III to adduct II in this process stage and eventually leads to the suppression of re-formation of the undesirable adduct III, so that when use is made of this recycling method, the overall balance of this cyclic process virtually displays only the desired adduct II and not its undesirable isomer III.

Alternatively, instead of recycling it to the partial reaction process stage a) of the process according to the invention, the adduct III can be isomerized in a separate isomerization process stage, by passing the adduct III separated from the adduct II through, eg, a reactor filled with one of the catalysts suitable for use in partial reaction a), separating the effluent from this reactor, which consists of the isomerization mixture of adduct III and adduct II formed therein, into adduct II and adduct III, for example, by distillation, processing the resulting adduct butyraldehyde and/or n-butanol in the remaining process stages of the process of the invention and recycling the adduct III back to the isomerization reactor.

The isomerization of the adduct III to adduct II in the isomerization reactor can take place in the presence or absence of a solvent. It is preferred to carry out this reaction without the use of solvents. If the isomerization is carried out in the presence of a solvent, those used are generally high-boiling solvents such as ethers, for example, di- or triethylene glycol dimethyl ether, di- or tri-ethylene glycol dibutyl ether, sulfoxides, eg, dimethyl sulfoxide or sulfones, such as sulfolane, high-boiling aromatic or aliphatic hydrocarbons or halogenated aliphatic or aromatic solvents, eg, dichlorobenzene. The use of low-boiling solvents is possible but usually entails an increase in energy expenditure during distillation of the effluent from the reactor to separate it into the adducts II and III.

In the continuation of the process of the invention for the preparation of n-butyraldehyde and/or n-butanol the adduct II is catalytically isomerized in the partial reaction c) to form the enol ether of formula IV, which is then catalytically hydrolyzed in partial reaction d) in the presence of water to form n-butyraldehyde and/or is catalytically converted to n-butanol in the presence of water and hydrogen. The reactions c) and d) in the process of the invention can be effected, as desired, successively in two process stages or successively in a single reactor or, particularly advantageously, as a one-shot process effected in a single process stage. Both reactions c) and d) can take place in the gaseous phase or in the liquid phase.

As just mentioned, the reactions c)—the isomerization of the adduct II to form the enol ether IV—and d)—its reaction with water or hydrogen and water to form n-butyraldehyde and/or n-butanol—are most preferably carried out in a single process stage. As a result, this process stage encompasses the following chemical reactions as depicted in the reaction equation (2)

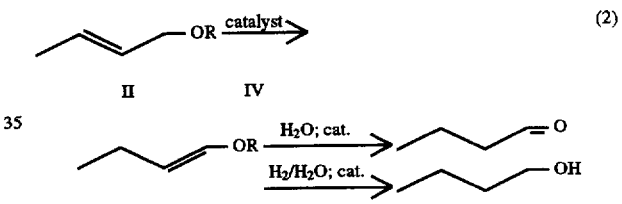

The last reaction step in each case, ie the hydrolysis of the enol ether IV to n-butyraldehyde on the one hand or the combined hydrolysis/hydrogenation of the enol ether IV to n-butanol on the other hand, can, by selecting appropriate reaction conditions, particularly by selecting a suitable catalyst and controlling the amount of the reactants water and hydrogen made available during the reaction, controlled in such a manner that either the end product n-butyraldehyde or the end product n-butanol is selectively formed or that mixtures of these two desired products are formed as end product of the process of the invention.

We have found, surprisingly, that the catalysts which catalyze the isomerization of the adduct II to the enol ether IV, generally also work well as catalysts for the hydrolysis of the enol ether IV to n-butyraldehyde or for the combined hydrolysis/hydrogenation of the enol ether IV to n-butanol. Accordingly, in the particularly preferred embodiment of the process of the invention, ie the execution of the reactions c) and d) in a single process stage, the same catalysts can be used both for the preparation of the end product n-butyraldehyde and for the preparation of the end product n-butanol.

Both the isomerization of the adduct II to the enol ether IV and the hydrolysis of the enol ether IV to n-butyraldehyde or the combined hydrolysis/hydrogenation of the enol ether IV to n-butanol can be carried out in the gaseous phase or in the liquid phase. When carrying out these reaction steps in a single process stage in the liquid phase both homogeneous and heterogeneous catalysts can be used. If these process stages are operated in the gaseous phase, heterogeneous catalysts are preferred in general.

The homogeneous catalysts used for the isomerization of the adduct II to the enol ether IV and its hydrolysis or combined hydrolysis/hydrogenation to n-butyraldehyde and/or n-butanol in a single process stage comprise a large number of transition metal element compounds, particularly those containing Group Ib, Vb, VIb, VIIb, and VIIIb elements, preferably copper, vanadium, chromium, molybdenum, tungsten, rhenium, iron, cobalt, nickel, ruthenium, rhodium, palladium, platinum, osmium and/or iridium.

Suitable catalysts are, for example, the salts of these transition metals, particularly their halides, nitrates, sulfates, phosphates, or carboxylates soluble in the reaction medium, for example, their $C_1$–$C_{20}$ carboxylates, such as formates, acetates, propionates, 2-ethylhexanoates, and also the citrates, tartrates, malates, malonates, maleates, or fumarates, sulfonates, for example, methanesulfonates, benzenesulfonates, naphthalenesulfonates, toluenesulfonates, or trifluoromethanesulfonates, cyanides, tetrafluoroborates, perchlorates, or hexafluorophosphates, also soluble salts of the oxy-acids of these metals, particularly the alkali metal, alkaline earth metal, or onium salts, such as ammonium, phosphonium, arsonium, or stibonium salts, of vanadium oxy-acids, rhenium oxy-acids, or perrhenic acid, or the anhydrides of these acids, particularly dirhenium heptoxide, soluble inorganic complex compounds of these elements, particularly their aquo, ammine, halo, phosphine, phosphite, cyano, or amino complexes as well as the complexes of these transition metals with chelating agents such as acetylacetone, dioximes, for example, diacetyldioxime, furildioxime, or benzildioxime, ethylenediaminetetraacetic acid, nitrilotriacetic acid, nitrilotriethanol, ureas or thioureas, bisphosphines, bisphosphites, bipyridines, terpyridines, phenanthrolines, 8-hydroxyquinoline, crown ethers or poly(alkylene glycol)s, as well as organometallic compounds of these transition metal elements, for example, carbonyl complexes such as HRuCl(CO)(PPh$_3$)$_3$,
HRuCl(CO)(hexyldiphenylphosphine)$_3$,
RuH$_2$(CO)(PPh$_3$)$_3$,
RuH$_2$(PPh)$_3$ or
IrCl(CO)(PPh$_3$)$_3$ the abbreviation PPh$_3$ designating triphenylphosphine, Fe$_2$(CO)$_9$ or Fe$_3$(CO)$_{12}$, organotrioxorhenium(VII) compounds such as $C_1$–$C_4$ alkyltrioxorhenium(VII), particularly methyltrioxorhenium(VII), cyclopentadienyltrioxorhenium (VII), or phenyltrioxorhenium(VII).

Preferred salt-like homogeneous catalysts are the halides, particularly the chlorides, nitrates, sulfates, sulfonates, carboxylates, and cyanides of rhodium, ruthenium, palladium, platinum, iridium, rhenium, and vanadium as well as the alkali metal, alkaline earth metal, ammonium, alkylammonium, arylammonium, arylphosphonium, and alkylphosphonium salts of vanadic acids, particularly their monovanadates, of rhenic acids, particularly their rhenates (IV), rhenates(VI) and perrhenates.

Another suitable homogeneous catalyst is dirhenium heptoxide (Re$_2$O$_7$).

Inorganic complex compounds preferably used in the process of the invention for carrying out the reactions c) and d) are, eg. ruthenium trichloride, rhodium trichloride, and iridium hexaquoditosylate.

Organo-transition-metal element compounds preferably used in the process of the invention as homogeneous catalysts for carrying out the reactions c) and d) are, eg. carbonyl complexes, such as HRh(PPh$_3$)$_3$(CO),
HRuCl(CO)(PPh$_3$)$_3$ or
RuCl$_2$(CO)$_2$(PPh$_3$)$_3$, as well as organotrioxorhenium compounds of the formula V

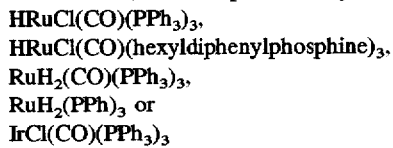

in which $R^1$ is a $C_1$–$C_{10}$ alkyl group, an unsubstituted cyclopentadienyl group or a cyclopentadienyl group substituted by 1 to 5 $C_1$–$C_4$ alkyl groups, a $C_6$–$C_{10}$ aryl group or a $C_7$–$C_{11}$ group. For information on the preparation of these organotrioxorhenium compounds reference is made to the processes described in Angew. Chem. 100, 420 (1988), Angew. Chem. 103, 183 (1991) 100, 4, J. Organomet. Chem. 297, C 5 (1985), Angew. Chem. 100, 1269 (1988) and J. Organomet. Chem. 382, 1 (1990).

Particularly preferred homogeneous catalysts for the execution of the reactions c) and d) in a single process stage are complexes of the transition metal elements mentioned above, particularly those of cobalt, nickel, rhodium, ruthenium, palladium, platinum, and iridium with monodentate or polydentate, particularly bidentate, phosphine or phosphite ligands and/or with nitrogenous ligands, in which the (—N=C—C=N—) structure unit is responsible for their property as chelating agent, for example, 2,2-bipyridine or 1,10-phenanthroline, as well as the ligands derived from these parent compounds by substitution or anellation.

Suitable phosphine ligands are, for example, those suitable for carrying out the partial reaction a) of the process of the invention and the phosphine ligands mentioned in this application in the description of said partial reaction, to which reference is made herewith. Examples of suitable 2,2-bipyridine or 1,10-phenanthroline ligands are those 2,2-bipyridine or 1,10-phenanthroline ligands mentioned in the description of the partial reaction a) as being suitable for carrying out said partial reaction a) of the process of the invention as well as their derivatives and structural analogs mentioned loc cit, to which reference is made herewith.

Suitable phosphite ligands are, eg. trialkylphosphites, alkyldiarylphosphites, triarylphosphites, alkylbisphosphites, arylbisphosphites, alkylarylbisphosphites. The alkyl group-carrying ligands may contain the same or different $C_1$–$C_{10}$, preferably $C_1$–$C_6$, alkyl or cycloalkyl groups. The aryl group-carrying ligands can contain the same or different $C_6$–$C_{12}$ groups, particularly the phenyl or naphthyl group, or alternatively the diphenyl group. Furthermore phosphite ligands can be used for complexing the transition metals, which carry heterocycloaliphatic groups, such as pyrrolidine, imidazolidine, piperidine, morpholine, oxazolidine, piperazine, or triazolidine groups or heteroaromatic groups, such as pyrrole, imidazole, oxazole, indole, pyridine, quinoline, pyrimidine, pyrazole, pyrazine, pyridazine, or quinoxazoline groups together with other alkyl or aryl groups. The alkyl or aryl groups of the phosphite ligands can be unsubstituted or can carry substituents which are inert under the reaction conditions, such as $C_1$–$C_4$ alkoxy, di-($C_1$–$C_4$ alkyl)amino, $C_1$–$C_6$ alkyl, hydroxy, nitro, cyano, or sulfonate groups. The sulfonate-substituted phosphite ligands and their complexes are generally water-soluble. Suitable phosphite ligands are, eg. trimethylphosphite, triethylphosphite, tripropylphosphite, triisopropylphosphite, tributylphosphite, tricyclopentylphosphite, tricyclohexylphosphite, triphenylphosphite as well as the mono- and bis-phosphite ligands described in EP-A 472,071, EP-A 213,639, EP-A 214,622, DE-A 2,733,796, EP-A 2,261, EP-A 2,821, EP-A 9,115, EP-A 155,508, EP-A 353,770, U.S. Pat. No. 4,318, 845, U.S. Pat. No. 4,204,997 and U.S. Pat. No. 4,362,830.

When carrying out the reactions c) and d) with catalysts comprising homogeneous phosphine or phosphite complexes soluble in the reaction medium it may be advantageous to add an additional phosphine or phosphite to the reaction mixture, preferably the phosphine or phosphite serving as ligand in the homogeneous catalyst employed. Such an addition can cause prolongation of the useful life of the homogeneous catalyst and moreover improve the selectivity of the isomerization of the adduct II toward the enol ether IV and the selectivity in the combined hydrolysis/ hydrogenation of the enol ether IV to n-butanol and thus the overall selectivity of the process. A similar advantageous effect can be induced by the addition of carbon monoxide to the reaction mixture, particularly when making use of carbonyl group-containing transition metal element complexes as homogeneous catalysts.

Although the addition of hydrogen to the reaction mixture is unnecessary for the preparation of the end product n-butyraldehyde, the feed of small amounts of hydrogen can, optionally together with the addition of small amounts of carbon monoxide when making use of carbonyl group-containing homogeneous catalysts, lead to a prolongation of the useful life of these homogeneous catalysts. Conveniently, synthesis gas can be used for this purpose.

To achieve the aforementioned effects, the phosphine or phosphite is in general added in a molar amount with respect to the phosphine or phosphite complex of the transition metal element of from 2 to 100 times, preferably from 2 to 20 times and more preferably from 2 to 5 times. If the transition metal element complex serving as homogeneous catalyst is produced in situ in the reaction mixture, it is advantageous to use a correspondingly high excess of phosphine or phosphite ligand over the respective transition metal element.

The homogeneous transition metal catalysts soluble in the reaction medium are generally employed in amounts of, preferably, from 0.05 to 0.2 mol % with respect to the adduct II fed to the reactor. It will be obvious to the person skilled in the art that the amount of homogeneous catalyst to be added is governed in each case by the catalytical activity of the homogeneous catalyst used. Depending on the nature of the homogeneous catalyst employed it will thus be advantageous to add a larger or smaller amount of catalyst to the reaction mixture. Advantageously the optimum amount is determined in a preliminary test for each homogeneous catalyst to be used.

The execution of the reactions c) and d) in a single process stage with the aid of the said homogeneous catalysts can be carried out batchwise, eg, in stirred vessels, or continuously, eg, in tubular reactors, at temperatures of in general more than 80° C. and under a pressure of generally from 5 to 100 bar, preferably from 10 to 60 bar. The isomerization of the adduct II to the enol ether IV and its convertion to n-butyraldehyde and/or n-butanol in a single process stage can take place in the presence or absence of added solvents, such as aliphatic or aromatic hydrocarbons, eg, toluene, benzene, or cyclohexane, alcohols, eg, butanols, particularly n-butanol, higher fatty alcohols or glycols, ethers, eg, dibutyl ether, tetrahydrofuran, dioxane or low molecular weight poly(alkylene glycol)s, halogenated aliphatic or aromatic hydrocarbons, eg, chloroform, dichloromethane, chlorobenzene, dichlorobenzene, sulfoxides, or sulfones, eg, dimethyl sulfoxide or sulfolane.

Instead of using these conventional solvents for the isomerization of the adduct II to the enol ether IV and its conversion to n-butyraldehyde and/or n-butanol it is possible to use a phosphine melt for this purpose. This mode of operation can be used to advantage when use is made of phosphine-containing catalysts. In general, the quasi solvent phosphine to be used is, theoretically, arbitrary, but it is in fact preferred to use, in the melt, that particular phosphine which serves as ligand in the transition metal element complex serving as homogeneous catalyst.

If no further solvents are added in the single-stage conversion of the adduct II to the end products n-butyraldehyde and/or n-butanol, the reactants themselves, ie the adduct II of the enol ethers IV and the water employed in the invention for the hydrolysis of the enol ether IV, and the end products of the reaction, cause dissolution of the homogeneous catalysts employed in accordance with the invention.

For the preparation of the end products n-butyraldehyde and n-butanol water is added to the reaction mixture in a molar ratio, based on adduct II fed to the reactor, generally of from 1:1 to 100:1 and preferably from 2:1 to 20:1 and more preferably from 5:1 to 10:1. When the process is carried out batchwise the water can be placed in the reactor together with the other reactants, the adduct II and the homogeneous catalyst, but it may be advantageous to meter the water to the reactor following commencement of the reaction. The decision as to which of these modi of operation is to be used will depend on the catalyst used in each case and the pressure and temperature conditions employed. Advantageously the optimum mode of operation is determined for each catalyst used in a preliminary test. Similarly, when the process is carried out continuously, eg, in a tubular reactor or a cascade of reactors, the water can be passed to the reactor together with the other reactants, or metered to the reactor via a separate inlet only after the reactants have resided in the reactor for a specific period of time.

If the desired end product is n-butanol, not only is water added to the reaction mixture for the hydrolysis of the enol ether IV, but also hydrogen is added in a molar ratio, based on adduct II added to the reactor, generally of from 1:1 to 100:1, preferably from 1:1 to 10:1 and more preferably from 1:1 to 2:1. This admixture can take place, when using a batch mode of operation, by forcing in the necessary amount of hydrogen into the reactor or by dispersing the hydrogen in the reaction medium, for example, by means of bubble-cap columns or by means of loop reactors equipped with nozzles for dispersing the hydrogen. The admixture of the hydrogen can take place when the reactor is charged with the other reactants, ie the adduct II, the water, and the homogeneous catalyst. Alternatively, the hydrogen, can be subsequently introduced into the reaction apparatus, advantageously following commencement of the reaction. The decision as to which of these modi will be used in each instance, will depend on the catalyst used and the pressure and conditions used in each case as well as on the design of the reactor. Conveniently, the optimum mode of operation is determined in a preliminary test. Similarly, when the process is carried out continuously, eg, in a tubular reactor, a bubble-cap column reactor or a packed column, the hydrogen can be introduced into the reactor together with the other reactants or else fed to the reactants in the reactor through a separate inlet after these have been present therein for a specific period of time.

If the desired end product is a mixture of n-butanol and n-butyraldehyde, the proportions of these products in the product mixture can be controlled, for example via the feed of hydrogen and/or the temperature of reaction used. If substoichiometric amounts of hydrogen are employed, only a portion of the starting material will, of course, be hydrogenated to n-butanol, and by using a lower temperature of reaction the velocity of the hydrogenation reaction can be slowed down to such a degree that only a portion of the starting material is hydrogenated to n-butanol.

On completion of the reaction, the reaction product is generally purified by distillation, whilst the homogeneous catalyst used is recovered from the bottoms of the distillation to be used again if desired, for example, by recycling the catalyst solution to the process stage involving the isomerization of the adduct II to the enol ether IV and its hydrolysis and hydrogenation. If recycling of the catalyst is desired in the process of the invention, a solvent can be added to the reaction mixture, advantageously, this preferably being a solvent which boils at a higher temperature than the reaction products n-butanol and n-butyraldehyde. If the homogeneous catalyst used is chemically and thermally stable under the conditions of the distillation, the addition of a high-boiling solvent can be dispensed with and the homogeneous catalyst can be recycled in solid form to the reaction. When purification is effected by distillation, the reaction product n-butyraldehyde and/or n-butanol is also separated from the alcohol ROH I liberated in the previous process stage from the enol ether IV by hydrolysis or hydrogenation, which is recycled to the first process stage of the process of the invention involving the addition of the alcohol ROH I to 1,3-butadiene. Valuable by-products of the process according to the invention can be obtained during purification, by distillation, of the reaction product, these being the octanols or dodecanols, or the aldehydes corresponding to these alcohols, formed as a result of the partial dimerization and trimerization of the butadiene.

In a particularly preferred embodiment of the process of the invention the isomerization of the adduct II to the enol ether IV and its hydrolysis or hydrogenation to n-butyraldehyde and/or n-butanol is carried out in a single process stage using a heterogeneous catalyst, whilst the process can be carried out either in the liquid phase or in the gaseous phase.

We have found, surprisingly, that the catalysts that can be used both for the isomerization of the adduct II to the enol ether IV and for the hydrolysis of the enol ether IV to n-butyraldehyde or for the combined hydrolysis/hydrogenation of the enol ether IV to n-butanol are commonly used heterogeneous hydrogenation catalysts substantially insoluble in the reaction medium. Of these hydrogenation catalysts those are preferred which contain one or more Group Ib, VIb, VIIb, and VIIIb elements, optionally in combination with one or more Group Vb elements, particularly copper, chromium, molybdenum, tungsten, rhenium, ruthenium, cobalt, nickel, rhodium, iridium, palladium, and/or platinum, optionally in combination with iron.

The more active hydrogenation catalysts such as nickel or the platinum metals can be advantageously doped with main group elements capable of acting as catalyst poisons, so as to partially poison such catalysts. This makes it possible to achieve a higher degree of selectivity in the combined hydrolysis/hydrogenation of the enol ether IV to n-butanol. Suitable main group elements are, eg, the chalcogenes, such as sulfur, selenium, and tellurium, as well as the elements phosphorus, arsenic, antimony, bismuth, tin, lead, and thallium.

In the process of the invention use can be made of, eg, so-called precipitation catalysts to act as the heterogeneous catalysts. Such catalysts can be prepared by precipitating their catalytically active components in the form of, eg, difficultly soluble hydroxides, oxide hydrates, basic salts, or carbonates from their salt solutions, particularly from solutions of their nitrates and/or acetates, for example, by the addition of solutions of alkali metal and/or alkaline earth metal hydroxide and/or carbonates, then drying the precipitates obtained and converting them, by calcination at generally from 300° to 700° C., particularly from 400° to 600° C., to the respective oxides, mixed oxides and/or oxides of mixed-valency, which are reduced, eg, by treatment with reducing agents, such as hydrogen or hydrogen-containing gases, at usually from 50° to 700° C, particularly at a temperature of from 100 to 400° C., to the respective metals and/or oxide compounds having a low degree of oxidation and are thus converted to the actual catalytically active form. During this process reduction is usually carried out until no more water is formed. In the preparation of precipitation catalysts, which contain a support material, the precipitation of the catalytically active components can take place in the presence of the respective support material. Alternatively however, the catalytically active components can be advantageously precipitated concurrently with the support material from the respective salt solutions.

In the process of the invention it is preferred to use hydrogenation catalysts in which the metals or metal compounds catalyzing the hydrogenation are present as deposits on a support material. Apart from the aforementioned precipitation catalysts, which contain a support material in addition to the catalytically active components, suitable catalysts for the process of the invention are generally those supported catalysts in which the catalytically effective components have been applied to a support material by, say, impregnation.

The manner in which the catalytically active metals are applied to the support is not usually important and can comprise a wide variety of methods. The catalytically active metals can be applied to these support materials, eg, by impregnation with solutions or suspensions of the salts or oxides of relevant elements, drying and then reducing the metal compounds to the respective metals or compounds of a lower degree of oxidation by means of a reducing agent, preferably with the aid of hydrogen, hydrogen-containing gases or hydrazine. Another possibility to effect application of the catalytically active metals on to these supports consists in impregnating the supports with solutions of thermally readily decomposable salts, eg, with nitrates or with thermally readily decomposable complex compounds, eg, carbonyl or hydrido complexes of the catalytically active metals, and heating the impregnated support to temperatures of from 300° to 600° C. for the purpose of thermally decomposing the adsorbed metal compounds. This thermal decomposition is preferably carried out under a blanket of protective gas. Suitable protective gases are, eg, nitrogen, carbon dioxide, hydrogen, or the noble gases. Furthermore the active metals can be deposited on to the catalyst support by vapor deposition or by flame spraying.

The content of catalytically active metals in these supported catalysts is theoretically irrelevant to the success of the process according to the invention. It will be apparent to the person skilled in the art that higher contents of catalytically active metals in these supported catalysts lead to higher space-time yields than lower contents. Generally however, supported catalysts are used whose content of catalytically active metals is from 0.1 to 80 wt % and preferably from 0.5 to 30 wt %, based on the total catalyst. Since these content figures refer to the total catalyst including support material, and since different support materials have very different specific weights and specific surface areas, these statements can be deviated from upwardly or downwardly without impairing the results of the process of the invention. Of course, a number of catalytically active metals can be applied to the respective support material if desired. Furthermore the catalytically active metals can be applied to the support, for example, by the processes described in DE-A 2,519,817, EP-A 147,219, and EP-A 285,420. In the catalysts described in the aforementioned references the catalytically active metals are present in the form of alloys, which are produced by thermal treatment and/or reduction of salts or complexes of the above metals deposited on a support by, eg, impregnation.

Activation of the precipitation catalysts and of the supported catalysts can also take place in situ in the reaction mixture due to the hydrogen present therein, however, these catalysts are preferably activated prior to use in the process of the invention.

Suitable support materials are generally the oxides of aluminum and titanium, zirconium dioxide, silicon dioxide, kieselguhr, silica gel, argillaceous earths, montmorillonites, silicates, such as magnesium or aluminum silicates, zeolites, such as ZSM-5 or ZSM-10 zeolite, and activated charcoal. Preferred support materials are aluminum oxides, titanium dioxides, zirconium dioxide, and activated charcoal. It is of course possible to use mixtures of different support materials as supports for catalysts to be used in the process of the invention, if desired.

Examples of suitable heterogeneous catalysts for execution of the reactions c) and d) in a single process stage are the following catalysts: platinum dioxide, palladium on aluminum oxide, palladium on silicon dioxide, palladium on barium sulfate, rhodium on activated charcoal, rhodium on aluminum oxide, ruthenium on silicon dioxide or activated charcoal, nickel on silicon dioxide, cobalt on silicon dioxide, cobalt on aluminum oxide, carbonyliron powder, rhenium black, Raney rhenium, rhenium on activated charcoal, rhenium/palladium on activated charcoal, rhenium/platinum on activated charcoal, copper on silicon dioxide, copper on aluminum oxide, copper on activated charcoal, copper on kieselguhr, copper on silica gel, copper on titanium dioxide, copper on zirconium dioxide, copper on magnesium silicate, copper on aluminum silicate, copper on montmorillonite, copper on zeolite, Raney copper, platinum oxide/rhodium oxide mixtures, platinum/palladium on activated charcoal, copper chromite, barium chromite, nickel/chromium oxide on aluminum oxide, dirhenium heptoxide ($R_2O_7$), cobalt sulfide, nickel Sulfide, molybdenum(VI) sulfide, copper/molybdenum(VI) oxide/silicon dioxide/aluminum oxide catalysts, palladium on activated charcoal catalysts partially poisoned with selenium or lead, and the catalysts described in DE-A 3,932,332, U.S. Pat. No. 3,449,445, EP-A 44,444, EP-A 147,219, DE-A 3,904,083, DE-A 2,321,101, EP-A 415,202, DE-A 2,366,264, and EP-A 100,406.

It may also be advantageous to use, in the process of the invention, hydrogenation catalysts containing Brönsted and/or Lewis acid centers.

The catalytically active metals themselves can act as Brönsted or Lewis acid centers if, for example, when effecting activation of the catalyst with hydrogen or hydrogenous gases, reduction to the respective metals is not carried to completion. This applies, eg, to the catalysts containing rhenium and chromite, such as supported rhenium catalysts and copper chromite. In the supported rhenium catalysts the rhenium is present in the form of a mixture of rhenium metal with rhenium compounds at higher oxidation stages, where the latter can display effects such as those shown by Lewis or Brönsted acids. Moreover, such Lewis or Brönsted acidic centers can be introduced into the catalyst via the support material used. As support materials containing Lewis or Brönsted acidic centers there may be mentioned, eg, the aluminum oxides, titanium dioxides, zirconium dioxide, silicon dioxide, the silicates, argillaceous earths, zeolites, and activated charcoal.

Thus we particularly prefer to use, in the process of the invention, as hydrogenation catalysts, supported catalysts which contain group Ib, VIb, VIIb, and/or VIIIb elements, particularly Group Ib, VIIb, and VIIIb elements deposited on a Brönsted or Lewis-acidic support material. Particularly advantageous catalysts are, eg, rhenium on activated charcoal, rhenium on zirconium dioxide, rhenium on titanium dioxide, rhenium on silicon dioxide, copper on activated charcoal, copper on silicon dioxide, copper on kieselguhr, copper on silica gel, copper on titanium dioxide, copper on zirconium dioxide, copper on magnesium silicate, copper on aluminum silicate, copper on fuller's earth, copper on zeolite, ruthenium on activated charcoal, ruthenium on aluminum oxide, ruthenium on silicon dioxide, ruthenium on magnesium oxide, ruthenium on zirconium dioxide, ruthenium on titanium dioxide, and also palladium on activated charcoal catalysts partially poisoned with selenium or lead.

Hydrogenation catalysts, which do not themselves have such Brönsted or Lewis acid centers, can be admixed with Lewis or Brönsted acidic components, such as zeolites, aluminum or silicon oxides, phosphoric acid or sulfuric acid. The latter are generally added in amounts of from 0.01 to 5 wt %, preferably from 0.05 to 0.5 wt % and more preferably from 0.1 to 0.4 wt %, based on the weight of the catalyst.

Other suitable heterogeneous catalysts for the isomerization of the adduct II to the enol ether IV and its hydrolysis or hydrogenation to n-butyraldehyde and/or n-butanol in a single process stage are those which contain in heterogenized form the complex compounds of Group Ib, VIb, VIIb, and VIIIb transition metal elements which can be used for the homogeneous catalysis of the complex compounds suitable for use in this process stage, for example, those in which the respective transition metal element is attached to a polymeric matrix.

Such polymeric matrices can be resins, such as styrene-divinylbenzene resins or phenol-formaldehyde resins, to which the respective ligands serving to chelate the transition metal element are preferably attached by covalent bonds, which again form complexes with the respective transition metals and thus quasi immobilize them. Such heterogenized, polymerically linked transition metal element complex catalysts with 2,2-bipyridine or 1,10-phenanthroline ligands or heterogenized phosphine or phosphite complexes of the catalytically active transition metal elements can be prepared, eg, by the prepublished processes mentioned above for the preparation of said catalysts in connection with the description of partial reaction a). Organotrioxorhenium (VII) catalysts can, eg, be attached by coordinate-bond linkage, by the process described in DE-A 3,902,357, to nitrogenous polymers, such as poly(vinyl pyrrolidone), poly (2-vinylpyridine), poly(2-vinylpyridine-co-styrene), poly (acrylic acid amide)s, polyimides, polyamides and polyurethanes and heterogenized in this way, and then used in the process of the invention as heterogeneous catalysts.

Using the said heterogeneous catalysts the isomerization of the adduct II to the enol ether IV and its hydrolysis or hydrogenation to n-butyraldehyde and/or n-butanol can be carried out in a single process stage continuously or batchwise.

If this reaction is carried out in the liquid phase, the heterogeneous catalyst can be used in the form of suspended solids in the liquid reaction medium or, preferably, disposed in a fixed bed or a number of fixed beds. When use is made of a heterogeneous catalyst suspended in the liquid reaction medium the process can be carried out, eg, in stirred vessels or loop reactors. When use is made of a heterogeneous catalyst in the form of a fixed bed the reaction mixture is in general passed through the fixed catalyst bed either upwardly or downwardly.

Both the hydrogenation of the enol ether IV and its hydrolysis or hydrogenation can be carried out in adiabatic or isothermal reactors. Generally the space velocity of the liquid reaction mixture relatively to the catalyst is equivalent to from 0.01 to 10, preferably from 0.05 to 6 and more preferably from 0.08 to 3 kg of ether per liter of catalyst per hour. When use is made of the heterogeneous catalysts the reaction can take place in the presence or absence of a solvent. Suitable solvents are the same as those which can be used when carrying out the process under homogeneous catalysis conditions.

As described above with reference to carrying out the reactions c) and d) of the process of the invention using homogeneous catalysis, the water required for the preparation of the end products n-butyraldehyde and/or n-butanol can be fed to the reactor together with the adduct II and/or added via separate feed lines, divided into one or more partial streams, and introduced into the catalyst bed at various points. The same applies to the feed of water and hydrogen for the preparation of the end product n-butanol.

The water required for the preparation of n-butyraldehyde when carrying out the process under heterogeneous catalysis conditions is fed to the reactor at such a rate that the molar ratio of water to the adduct II added is generally from 1:1 to 100:1, preferably from 1:1 to 70:1 and more preferably from 1:1 to 30:1. The combined isomerization of the adduct II to the enol ether IV and its hydrolysis to n-butyraldehyde in a single process stage over a heterogeneous catalyst in the liquid phase is generally carried out at a temperature of from 20° to 400° C., preferably from 30° to 350° C. and more preferably from 80° to 300° C. and under a pressure of, in general, from 1 to 300 bar, preferably from 2 to 150 bar, and more preferably from 5 to 100 bar.

The hydrogen required, in addition to water, for the preparation of n-butanol when carrying out the process under heterogeneous catalysis conditions is fed to the reactor at such a rate that the molar ratio of hydrogen added to adduct II added is generally from 1:1 to 100:1, preferably from 1.5:1 to 80:1, and more preferably from 2:1 to 40:1. The combined isomerization of the adduct II to the enol ether IV and its hydrolysis/hydrogenation to n-butanol in a single process stage in a heterogeneous catalyst system in the liquid phase is generally carried out at a temperature of from 20° to 400° C., preferably from 30° to 350° C. and more preferably from 80° to 300° C. and under a pressure of generally from 1 to 300 bar, preferably from 5 to 250 bar, and more preferably from 20 to 200 bar. Of course, the quantity of water required for the preparation of n-butanol from the adduct II is the same as that required for the preparation of n-butyraldehyde from the adduct II.

If the desired end product is a mixture of n-butyraldehyde and n-butanol, water and hydrogen are introduced at rates similar to those mentioned above and relate to the rate of feed of the adduct II such that the isolation of the two end products in the desired product ratio is possible. Moreover the ratio of these two end products in the effluent can also be set by using different heterogeneous catalysts, for example, by using heterogeneous catalysts which possess high hydrolysis activity and, in comparison, relatively low hydrogenation activity. This purpose can be advantageously realized, for example, by using catalysts which have been inactivated or partially poisoned with regard to their hydrogenating properties, eg, palladium on activated charcoal catalysts partially poisoned with selenium or lead.

The liquid effluent from this process stage is generally worked up by distillation, in a manner similar to that described above with reference to the execution of this process stage using homogeneous catalysts. Of course recycling of the catalyst, which may possibly be convenient and advantageous when using homogeneous catalysts, is omitted when using heterogeneous catalysts. Recycling of the alcohol ROH I liberated in this process stage back to the process stage involving the addition of the alcohol ROH I to 1,3-butadiene can be advantageously carried out in a manner similar to that already described with reference to the reaction occurring in this process stage using homogeneous catalysts.

As already mentioned, the isomerization of the adduct II to the enol ether IV and its hydrolysis or hydrogenation to n-butyraldehyde and/or n-butanol in a single process stage can be advantageously carried out in the gaseous phase. To this end conventional reactors for gas phase reactions are used, for example, those in which the catalyst is in the form of a fixed bed or fluidized bed. The reactors can be operated adiabatically or isothermally. When use is made of a fixed bed catalyst system, the catalyst can be disposed in a single fixed bed or, advantageously for the purpose of improving the dissipation of the heat of reaction, in a number of fixed beds, for example, in from 2 to 10 and preferably from 2 to 5 fixed beds. When making use of a number of fixed catalyst beds or when employing an adiabatic mode of operation of the reactor it may be advantageous to use intra-bed cooling of the reaction gas and/or to effect a temperature decrease of the reaction gas as it leaves one bed but before it reaches the next bed by injecting additional amounts of cool reactants such as hydrogen, water, adduct II, or enol ether IV between the individual fixed beds, in order to increase the selectivity of the reaction. Advantageously, when use is made of a number of fixed beds, the reaction in the individual fixed beds except for the last fixed bed is only allowed to reach partial conversion, for example, a conversion of from 50 to 98%. The reaction gases can be diluted if desired with a gas inert under the reaction conditions, such as nitrogen, saturated hydrocarbons, or argon.

The water required for the preparation of the end product n-butyraldehyde when carrying out the process in the gaseous phase is metered into the reactor at a rate in relation to the rate of input of the adduct II such that the molar ratio of water added to adduct II added is generally from 1:1 to 100:1, preferably from 1:1 to 70:1 and more preferably from 1:1 to 30:1. The water can be fed to the reactor together with the adduct II and/or, as described above, divided into a number of partial streams and introduced at different points of the reactor. Generally the space velocity of the reaction gas, essentially containing the adduct II, water, and possibly an inert gas, is from 0.01 to 10, preferably from 0.05 to 5 and more preferably, from 0.07 to 3 kg of reaction gas per liter of catalyst per hour. The reaction, encompassing the isomerization of the adduct II to the enol ether IV and its hydrolysis, is generally carried out at a temperature of from 70° to 400° C., preferably from 90° to 350° C. and more preferably from 110° to 330° C. and under a pressure of in general from 0.5 to 100 bar, preferably from 0.8 to 20 bar and more preferably from 1 to 10 bar.

The hydrogen required for the preparation of the end product n-butanol in addition to water, when carrying out the process in the gaseous phase, is fed to the reactor at a rate relative to the rate of feed of the adduct II such that the molar ratio of hydrogen added to adduct II added is in general from 1:1 to 200:1, preferably from 1.5:1 to 80:1 and more preferably from 2:1 to 40:1 . Hydrogen can be fed to the reactor together with the adduct II and/or, as described above, divided into a number of partial streams and fed in at various points of the reactor. Generally the space velocity of the reaction gas, essentially containing the adduct II, water, hydrogen, and possibly an inert gas, is from 0.01 to 10, preferably from 0.05 to 5, more preferably from 0.07 to 3 kg of reaction gas per liter of catalyst per hour. The reaction, encompassing the isomerization of the adduct II to the enol ether IV and its combined hydrolysis/hydrogenation, is generally carried out at temperatures of from 20° to 400° C., preferably from 100° to 350° C. and more preferably from 150° to 300° C. and under a pressure generally of from 0.5 to 100 bar, preferably from 0.9 to 50 bar, and more preferably from 1 to 30 bar.

In a manner similar to that described above with reference to the isomerization of the adduct II to the enol ether IV and its hydrolysis or hydrogenation to n-butyraldehyde and/or n-butanol in the liquid phase using heterogeneous catalysts, the reaction in the gaseous phase can be controlled by the feed of a mixture containing specific amounts of water and hydrogen, and by selecting the catalyst to be used such that the effluent from this process stage contains n-butyraldehyde and n-butanol in the desired proportions.

In order to work up the gaseous effluent it is advantageous to pass this, optionally after depressurization to atmospheric pressure, directly to a distillation apparatus where it is separated by distillation into its constituent parts.

The catalysts which can be used for the isomerization of the adduct II to the enol ether IV and its hydrolysis or hydrogenation to n-butyraldehyde and/or n-butanol in the gaseous phase in a single process stage are basically the same heterogeneous catalysts as those employed in the same reaction in the liquid phase. Preferably purely inorganic, mineral catalysts are used in the gas phase process. Preferred catalysts are, for example, supported catalysts containing Group Ib, VIb, VIIb , and/or VIIIb elements, optionally in combination with more or more Group Vb elements, particularly Group Ib , VIIb , and VIIIb elements present as deposits on a Brönsted or Lewis acidic support material. Particularly advantageous catalysts are, eg, rhenium on activated charcoal, rhenium on zirconium dioxide, rhenium on titanium dioxide, rhenium on silicon dioxide, copper on activated charcoal, copper on silicon dioxide, copper on kieselguhr, copper on silica gel, copper on titanium dioxide, copper on zirconium dioxide, copper on magnesium silicate, copper on aluminum silicate, copper on fuller's earth, copper on zeolite, ruthenium on activated charcoal, ruthenium on silicon dioxide, ruthenium on aluminum oxide, ruthenium on zirconium dioxide, ruthenium on magnesium oxide, and ruthenium on titanium dioxide; and also palladium on activated charcoal catalysts partially poisoned with selenium or lead.

A further advantageous embodiment of the isomerization of the adduct II to the enol ether IV and its hydrolysis or hydrogenation to n-butyraldehyde and/or n-butanol in a single process stage using heterogeneous catalysts can be achieved both when use is made of the liquid phase process and when use is made of the gas phase process and when making use of a single fixed bed for carrying out these reactions, by employing a combined catalyst bed, consisting of at least 2 layers of different heterogeneous catalysts which differ in activity and possibly selectivity for the two reactions c) and d), such that, eg, in the first layer, ie that nearest the reactor inlet, the adduct II is initially isomerized with high activity and selectivity to the enol ether IV, which then on passing through the next layer or layers, ie that or those nearest the outlet of the reactor and containing catalysts having lower isomerization activity but higher hydrolysis activity and/or higher hydrogenation activity is converted to n-butyraldehyde and/or n-butanol at a high degree of activity and selectivity.

By using a number of contiguous layers of variously active and/or selective catalysts it is possible to achieve accurate control of the heat generated during hydrolysis or the combined hydrolysis/hydrogenation of the enol ether IV, by which means the overall selectivity of the reaction can be increased. This effect can be intensified by eg, introducing the reactants water and/or hydrogen into the reactor separately from the adduct II at that zone of the catalyst bed where the hydrolysis or the combined hydrolysis/ hydrogenation takes place. The water and the hydrogen can be passed together to the respective zones of the catalyst bed or alternatively individually to different zones of the catalyst bed. Instead of using a combined bed containing all of the different catalysts required for catalyzing the individual reactions, it is possible, in this embodiment, to have the catalysts present in a number of fixed beds, each containing a different catalyst.

Although the execution of the reactions c) and d) of the process according to the invention in a single process stage, eg, by the methods described above is a preferred embodiment of the process of the invention, it may be advantageous under certain circumstances to carry out the individual reactions, ie the isomerization of the adduct II to the enol ether IV, the hydrolysis of the enol ether IV to n-butyraldehyde or the hydrogenation of the butyraldehyde to n-butanol, in a number of process stages. For example, it is possible to carry out each one of these reactions in an individual process stage by first isomerizing the adduct II to the enol ether IV in one process stage, then hydrolyzing the enol ether IV to n-butyraldehyde and then hydrogenating the n-butyraldehyde to n-butanol. Likewise the isomerization of the adduct II to the enol ether IV can take place in a separate process stage and the enol ether IV can then be hydrolyzed to n-butyraldehyde or be further processed in a hydrolysis/ hydrogenation reaction to n-butanol or a mixture of n-butanol and n-butyraldehyde. A further variant of the process according to the invention comprises carrying out the isomerization of the adduct II to the enol ether IV and its hydrolysis to n-butyraldehyde in a single process stage and then hydrogenating the n-butyraldehyde thus obtained to n-butanol in a further process stage.

When the partial reactions c) and d) are distributed over a number of process stages a wide variety of operational modi can be used in the individual process stages. For example, the isomerization of the adduct II to the enol ether IV can be carried as desired under homogeneous catalysis conditions or over heterogeneous catalysts. Also the hydrolysis or the combined hydrolysis/hydrogenation of the enol ether IV to n-butyraldehyde and n-butanol can be carried out either: in the liquid phase using homogeneous catalysts or heterogeneous catalysts or: in the gaseous phase.

When the individual partial reactions c) and d) are distributed over a number of process stages it is also possible to use, in the individual process stages, instead of the catalysts described above, which catalyze both the isomerization of the adduct II to the enol ether IV and its hydrolysis and hydrogenation, catalysts which can catalyze only the respective partial reaction. Thus the enol ether IV can be hydrolyzed, for example, by means of Brönsted acid catalysts, such as mineral acids, eg, hydrohalic acids, sulfuric acid, dilute nitric acid, phosphoric acid, or heterogeneous Brönsted acids, such as ion exchangers, zeolites, fuller's earths, or acid phosphates, for example, aluminum phosphates, to n-butyraldehyde or the n-butyraldehyde obtained, or the n-butyraldehyde obtained in a single process stage by isomerization of the adduct II to the enol ether IV and its hydrolysis, can be converted to n-butanol using catalysts which have only hydrogenation activity but no hydrolysis activity. Similarly there can be used in this case for the execution of the partial reaction c) an isomerizing catalyst which possesses neither hydrolysis activity nor hydrogenation activity.

The alcohol ROH I liberated during hydrolysis or combined hydrolysis/hydrogenation of the enol ether IV is preferably recycled back to the reaction defined as partial reaction a). On account of the possibility of splitting the partial reactions of the isomerization of the adduct II to the enol ether IV and its hydrolysis or its combined hydrolysis/hydrogenation up into a number of process steps, a higher degree of flexibility is obtained when constructing a plant for carrying out the process of the invention, by which means considerable savings can be effected.

BRIEF DESCRIPTION OF THE DRAWINGS
(FIG. 1)

The process of the invention is described in greater detail with reference to the flow sheet shown in the drawing which diagramatical represents an advantageous embodiment of the process of the invention, in which the addition of the alcohol ROH to 1,3-butadiene and the isomerization of the adduct II to the enol ether IV and its hydrolysis or combined hydrolysis/hydrogenation to n-butyraldehyde and n-butanol are both carried out in a single process stage in the liquid phase. Since the purpose of this process flow sheet is merely to illustrate the routing of the educt, intermediate and product streams in the process of the invention, obvious details of the plant, such as pumps, heat exchangers, valves, or relays, have been omitted from the process flow sheet for the sake of clarity.

Via the feed line 1 a mixture of 1,3-butadiene and alcohol :ROH I, preferably n-butanol, is fed to the reactor 2. The feed line 1 is charged with 1,3-butadiene and the alcohol ROH I via the feed lines 3 and 4 respectively. In the reactor 2 the alcohol ROH I is added to 1,3-butadiene catalytically, preferably by means of a Brönsted acid, in particular by means of an acid cation exchanger, which generally leads to the formation of a mixture of the adducts II and III. The effluent from the reactor 2, which substantially consists of the adducts II and III, higher-boiling butadiene derivatives, and unconverted 1,3-butadiene and alcohol ROH I, is passed through line 5 to the gas/liquid separator 6, in which gaseous 1,3-butadiene is separated from the liquid constituents of the effluent from reactor 2 and is either recycled back to the reactor 2 via the lines 7, 8 and 1 or is fed via the lines 7 and 9 to the flare to undergo combustion. The liquid mixture which settles in the separator 9 is passed via line 10 to the distillation column 11, in which the readily volatile adduct III is separated, by distillation, from the more difficultly volatile adduct II as well as any alcohol ROH I present and higher-boiling butadiene derivatives. The adduct III, unconverted alcohol ROH I and any unconverted 1,3-butadiene still present are then recycled via the lines 12 and 1 to the reactor 2, where the adduct III is isomerized in the presence of freshly added 1,3-butadiene and alcohol ROH I to form the adduct II. The low-boiling compound's fed together with the effluent from reactor 2 to the column 11, eg. vinylcyclohexene, are, if desired together with the residual butadienes separated in column 11, passed through outlet 42 to the flare. Instead of a single distillation column 11 there can be used, if desired, a number of distillation columns connected in line for effecting separation of the liquid effluent from reactor 2. When making use of a number of distillation columns instead of a single distillation column 11 higher-boiling reaction products contained in the effluent from reactor 2, for example, dibutyl ether and possibly alkoxy octadienes or alkoxy dodecatrienes, can be separated from the adduct II and removed from the process.

The liquid effluent coming from column 11 and which has been freed from the readily volatile adduct III and low-boiling and possibly higher-boiling by-products is fed via line 13 to the reactor 14, in which the adduct II is isomerized to the enol ether IV in a single process stage in the presence of a homogeneous or heterogeneous transition metal catalyst, which enol ether IV is hydrolyzed to n-butyraldehyde or, in a combined hydrolysis/hydrogenation stage, converted to n-butanol and, if desired, n-butyraldehyde. Hydrogen required for this reaction is fed to the reactor 14 via line 15 and the necessary water is added through line 16. Alternatively, instead of effecting the introduction via the feeds 15 and 16 the water or the hydrogen can be introduced to the reactor via the feeds 17 and 18. If it is desired to produce only n-butyraldehyde in the plant, the hydrogen lines 15 or 18 can remain closed or these lines can be used to admit only sufficient hydrogen to the reactor as is necessary to improving the useful life of the catalyst. If desired, carbon monoxide can be introduced into the reactor together with the hydrogen for the same purpose.

The liquid effluent from reactor 14, which contains essentially n-butyraldehyde and n-butanol, higher-boiling butadiene derivatives, for example, octanols or dodecanols, and possibly excess water as well as, if a homogeneous catalyst has been used in the reactor 14, catalyst solution, is passed through line 19 to the distillation column 20. The major part of the unconverted hydrogen is withdrawn from the reactor 14 via line 21 and is either recycled via the lines 15 or 18 back to the reaction or is flared off. The hydrogen can if desired be separated off in a gas/liquid separator installed between the reactor 14 and the distillation column 20 and be further treated as described above.

In the distillation column 20 the effluent from reactor 14 is separated by distillation into its constituent parts. The more readily volatile n-butyraldehyde is withdrawn as overheads via line 22 possibly together with low-boiling by-products and passed to an additional destillation stage (not shown) for the purpose of further purification. Freshly formed n-butanol is removed from the column via line 23 and passed on through line 24 for further use. Higher-boiling products, for example, dibutyl ether, octanols and dodecanols are removed from the column 20 through a number of outlets in its lower region, represented by the single outlet 26 in the drawing. If a homogeneous catalyst has been used in the reactor 14, the catalyst solution is removed from the bottoms of the column 20 via line 27 and, optionally after removal of a partial stream of spent catalyst via line 28 and replenishment with fresh catalyst solution via line 29, recycled to the reactor 14.

The reaction in the reactor 14 can if desired be controlled in such a manner that n-butanol but no n-butyraldehyde is produced therein. In another embodiment of the process of the invention n-butyraldehyde can be produced in the reactor 30 connected in parallel to the reactor 14 and supplied with a partial stream of the effluent from column 11 via line 31. In a manner similar to the procedure in the reactor 14 the adduct II is isomerized in a single process stage to the enol ether IV in the reactor 30 and said enol ether is hydrolyzed to n-butyraldehyde but not hydrogenated to n-butanol. The water required for carrying out hydrolysis in the reactor 30, is, depending on the nature and arrangement of the catalyst in reactor 30, introduced via the feed lines 32 and 33. The liquid effluent from reactor 30 passes through line 34 to the distillation column 35, from which n-butyraldehyde is withdrawn via line 36. The n-butanol liberated from the enol ether IV during hydrolysis or the alcohol ROH I used instead of n-butanol in reactor 2 is withdrawn from the column via line 37 and recycled via the lines 25 and 1 back to the reactor 2, where it is again caused to react with fresh 1,3-butadiene to form the adducts II and III. Higher-boiling products, for example, dimeric and trimeric butadiene derivatives, are removed through a number of outlets, represented by outlet 38 in the drawing, in the lower region of column 35. If a homogeneous catalyst has been employed in reactor 30, the catalyst solution is withdrawn from the bottoms of the column 35 via line 39, and, optionally following removal of a partial stream of spent catalyst via line 40 and replenishment with fresh catalyst solution via line 41, returned to the reactor 30.

When making use of n-butanol as the alcohol ROH I, according to a preferred embodiment of the process of the invention, the n-butanol isolated in column 20 and removed via line 23, which consists of n-butanol freshly formed from 1,3-butadiene and the n-butanol originally added via line 4 and liberated in reactor 14, is divided into two partial streams, the amount of freshly formed n-butanol being passed on through line 24 for further use and the original amount of n-butanol employed as alcohol ROH I being recycled via the lines 25 and 1 back to the reactor 2. When making use of an alcohol ROH I other than n-butanol this is removed from the column 20 through a separate outlet 43 positioned at a point appropriate to its boiling point and is recycled through the lines 25 and 1 back to the reactor 2.

The n-butanol withdrawn from column 20 via line 23 or optionally the alcohol ROH I differing from n-butanol and removed via outlet 43, are if necessary, prior to further use thereof or recycling thereof to the reactor 2, subjected to further purification by distillation (not shown in the drawing), in order to remove any impurities contained therein, such as dibutyl ether, and residual amounts of water from the reaction in reactor 14. The same applies to the supplementary purification, by distillation, of the higher-boiling products withdrawn via outlet 26. Purification by distillation of the alcohol ROH I withdrawn via line 43 or the n-butanol withdrawn via line 23 may be necessary in order to avoid an increase in the concentration of impurities and water in the circuit. The purification by distillation of the effluents from column 20 can take place by conventional destillation techniques and is not the subject of the present invention. Similar considerations apply to the products withdrawn from column 35 via the lines 36, 37 and 38. In this context we again point out that the outlets of the columns 11, 20 and 35 are drawn purely diagrammatically in the accompanying figure. The composition of the products to be distilled in these columns varies according to the mode of operation used in the reactors 2, 14 and 30 and it is a routine task for the person skilled in the art to appropriately dimension the distillation column necessary for the separation of the products with regard to the proportions of the products present.

EXAMPLES

Example 1

(partial reaction a))

A stirred autoclave having a capacity of 0.3 L was filled with 67.0 g (0.90 mol) of n-butanol and 15.0 g of Lewatit® SCS 118 in the H$^+$ form, which had been washed with water and n-butanol. 47.9 g (0.88 mol) of 1,3-butadiene were then forced into the reactor. After a reaction time of 10 h at a temperature of 90° C. and a pressure of 9 bar there was found, at a conversion rate of 46%, a selectivity toward 3-butoxybutene-1 of 48.4% and a selectivity toward 1-butoxybutene-1 of 41.1%.

Example 2

A stirred autoclave having a capacity of 0.3 L was filled with 67 g (0.90 mol) of n-butanol as well as with 11.5 g of Lewatit® SCS 118 in the H$^+$ form, which had previously been washed with water and n-butanol, and with 3.5 g of a Lewatit® SCS 118 ion exchanger doped with copper(II) chloride. 47.0 g (0.88 mol) of 1,3-butadiene were then forced into the autoclave. After 10 h of reaction at 90° C. and under autogenous pressure there was obtained, at a conversion rate of 69.1%, a selectivity of 46.8% toward 3-butoxybutene-1 and a selectivity of 44.3% toward 1-butoxybutene-2.

Example 3

A heated tubular reactor having a capacity of 1.4 L was charged with 1 kg of a gel-like ion exchanger of the trade name Amberlite® IR, 120 in the H$^+$ form which had been washed with water and n-butanol. 1,3-butadiene and n-butanol were mixed in the liquid phase under a pressure of 20 bar upstream of the reactor and then passed continuously through the ion exchanger bed. The influence of the reaction parameters: temperature, rate of flow, and molar ratio of 1,3-butadiene to n-butanol was examined over a wide range. The results obtained under the various test conditions are listed in Table 1. The analysis of the products was carried out by means of calibrated gas chromatography.

TABLE 1

Continuous addition of n-butanol to butadiene

| Rat of flow of | | | | Conversion | Selectivity [%] | | | | | |
|---|---|---|---|---|---|---|---|---|---|---|
| Butanol [g/h] | Butadiene [g/h] | Pressure [bar] | Temp. [°C.] | of butadiene [%] | 3-Butyoxy-butene-1 | 1-Butoxy-butene-2 | Butoxy-octadiene | Rem.[1] | Sum Oct.[2] VCH[3] | Unknown compnds |
| 81.5 | 46.0 | 20 | 91 | 65.1 | 40.5 | 36.4 | 11.5 | 4.5 | 1.9 | 5.2 |
| 83.9 | 39.2 | 20 | 80 | 39.3 | 51.0 | 36.8 | 8.6 | 0.8 | 2.0 | 0.8 |
| 49.0 | 26.2 | 20 | 80 | 57.0 | 49.2 | 37.7 | 9.5 | 1.1 | 1.4 | 1.1 |
| 59.1 | 18.9 | 20 | 80 | 49.9 | 52.1 | 39.1 | 6.6 | 0.4 | 1.0 | 0.8 |
| 49.0 | 13.5 | 20 | 80 | 72.0 | 50.0 | 40.1 | 7.1 | 0.7 | 1.0 | 1.1 |
| 147.9 | 44.5 | 20 | 111 | 72.4 | 42.2 | 43.3 | 8.1 | 1.5 | 1.7 | 3.2 | remainder[1] = sum of the compounds butoxydodecatriene dibutoxybutane dibutoxyoctene dodecatetraene
Oct.[2] octatriene
VCH[3] vinylcyclohexene Example 4

In a stirred autoclave having a capacity of 0.3 L routine tests for the addition of n-butanol to 1,3-butadiene were carried out under the reaction conditions stated in Tables 2, 3 and 4, the results thereof being as listed in said tables. Table 2 relates to the use of various acidic, undoped ion exchangers as catalysts, Table 3 gives the results of tests in which different amounts of undoped Lewatit® SCS 118 ion exchanger in admixture with Lewatit® SCS 118 ion exchanger doped with copper(II) chloride were used as catalysts, and Table 4 lists the results obtained when using mixtures of ion exchangers doped with different copper(II) salts with the respective undoped ion exchangers, as catalysts.

TABLE 2

Addition of n-butanol to butadiene using acid ion exchangers

| Ion Exchanger | Butanol [mol] | Butadiene [mol] | Temp. [°C.] | Reaction time [h] | Conversion [%] | Selectivities [%] | | | | | |
|---|---|---|---|---|---|---|---|---|---|---|---|
| | | | | | | 3-Butoxy-butene-1 | 1-Butoxy-butene-2 | Butoxy-octadienes | Oct[1] VCH[1] | Re-mainder | Unidentified compnds |
| GELATINOUS | | | | | | | | | | | |
| Lewatit® S 100 | 0.90 | 0.88 | 100 | 6 | 17.6 | 35.6 | 39.9 | 3.3 | 12.6 | 0.2 | 8.5 |
| Lewatit® SC 102 | 0.90 | 0.90 | 100 | 6 | 43.4 | 50.3 | 35.8 | 6.0 | 5.6 | 0.2 | 2.1 |
| Lewatit® SC 104 | 0.90 | 0.87 | 100 | 6 | 49.9 | 49.4 | 37.5 | 7.0 | 3.7 | 0.4 | 2.1 |
| Dowex® 50 W 4 | 0.90 | 0.88 | 100 | 6 | 45.2 | 50.9 | 37.8 | 2.7 | 6.2 | 0.0 | 2.4 |
| Amberlyst® IRN 77 L | 0.90 | 0.97 | 110 | 6 | 66.4 | 41.3 | 36.8 | 9.3 | 2.4 | 0.9 | 9.0 |
| Amberlyst® IRN 77 L | 0.90 | 0.91 | 100 | 6 | 71.3 | 42.2 | 36.8 | 9.6 | 2.4 | 1.2 | 7.7 |
| Amberlyst® IRN 77 L | 0.90 | 0.43 | 100 | 6 | 63.8 | 46.4 | 39.9 | 1.4 | 2.3 | 0.2 | 9.7 |
| Amberlite® IR 120 | 0.90 | 0.93 | 100 | 6 | 28.8 | 38.4 | 38.4 | 4.7 | 14.4 | 0.0 | 4.1 |
| Amberlite® | 0.90 | 0.87 | 100 | 6 | 52.6 | 45.7 | 41.2 | 8.0 | 2.7 | 0.7 | 1.7 |
| MACROPOROUS | | | | | | | | | | | |
| Lewatit® SPC 108 | 0.90 | 0.95 | 100 | 6 | 58.9 | 43.3 | 39.2 | 10.6 | 2.8 | 1.2 | 2.7 |
| Lewatit® SPC 112 | 0.90 | 0.89 | 100 | 6 | 59.3 | 40.4 | 38.4 | 12.0 | 2.1 | 2.0 | 5.2 |
| Lewatit® SPC 118 | 0.90 | 0.88 | 90 | 10 | 46.0 | 48.4 | 41.1 | 3.3 | 4.2 | 0.1 | 3.0 |
| Amberlyst® 15 | 0.90 | 0.78 | 100 | 6 | 63.9 | 42.8 | 41.0 | 9.8 | 1.4 | 0.7 | 4.3 |
| Amberlite® 200 | 0.90 | 0.88 | 100 | 6 | 64.3 | 44.8 | 39.5 | 6.9 | 4.5 | 0.4 | 3.9 |
| Amberlite® 252 | 0.90 | 0.81 | 100 | 6 | 54.5 | 45.2 | 38.5 | 7.3 | 6.5 | 0.0 | 2.6 |

TABLE 2-continued

Addition of n-butanol to butadiene using acid ion exchangers

| Ion Exchanger | Butanol [mol] | Butadiene [mol] | Temp. [°C.] | Reaction time [h] | Conversion [%] | Selectivities [%] | | | | | |
|---|---|---|---|---|---|---|---|---|---|---|---|
| | | | | | | 3-Butoxy-butene-1 | 1-Butoxy butene-2 | Butoxy-octadienes | Oct[1] VCH[1] | Re-mainder | Unidentified compnds |
| POWDER Bayer Cat. K 1481 | 0.90 | 0.87 | 90 | 10 | 71.4 | 46.4 | 36.1 | 7.0 | 3.0 | 0.2 | 7.3 |

[1])Sum of octatrienes and vinyl cyclohexene
Capacity of autoclave: 0.3 L Selectivity and conversion based on butadiene
Remainder = butoxydodecatrienes, dibutoxybutane, dodecatraenes
Autogenous pressure 15 g of ion exchanger in H⁺ form

TABLE 3

Addition on n-butanol to butadiene with $CuCl_2$-doped Lewatit ® SPC 118

| H⁺ form [g] | $CuCl_2$ form [g] | Conversion [%] | Selectivities [%] | | | | | | | |
|---|---|---|---|---|---|---|---|---|---|---|
| | | | 3-butoxy butene-1 | 1-Butoxy butene-2 | Butoxy-octadienes | Butoxy-dodecatrienes | Dibutoxy-butane | Oct[1] VCH[1] | Dodeca-tetraene | unidentified compounds |
| 15.0 | 0.0 | 46.0 | 48.4 | 41.1 | 3.3 | 0.0 | 0.0 | 4.2 | 0.1 | 3.0 |
| 14.0 | 1.0 | 56.7 | 47.3 | 43.6 | 4.0 | 0.1 | 0.1 | 3.7 | 0.2 | 0.9 |
| 11.5 | 3.5 | 69.1 | 46.8 | 44.3 | 4.0 | 0.1 | 0.0 | 4.1 | 0.1 | 0.7 |
| 10.0 | 5.0 | 59.4 | 46.7 | 43.6 | 3.1 | 0.0 | 0.0 | 6.0 | 0.1 | 0.4 |
| 5.0 | 10.0 | 42.9 | 45.5 | 40.3 | 2.5 | 0.0 | 0.0 | 9.6 | 0.1 | 2.0 |
| 0.0 | 15.0 | 10.8 | 23.7 | 15.2 | 0.0 | 0.0 | 0.0 | 52.6 | 0.0 | 8.5 |

Capacity of autoclave: 0.3 L: autogenous pressure, 90° C., 10 h reaction time
Selectivity and conversion based on butadiene Lewatit ® SCS 118 in H⁺ or Cu form rinsed with water and butanol
0.90 mol of butadiene
0.90 mol of butanol
Lewatit ® SCS 118

TABLE 4 addition of n-butanol to butadiene with $CuX_2$-doped ion exchangers

| 11.5 g of ion exchanger in the H⁺ form | 3.5 g of ion exchanger con-taining $CuX_2$ | Conversion [%] | selectivites [%] | | | | | | | |
|---|---|---|---|---|---|---|---|---|---|---|
| | | | 3-butoxy-butene-1 | 1-butoxy-butene-2 | butoxy-octa-dienes | butoxy-dodeca-trienes | dibutoxy-butane | Oct[1] VCH[1] | Dodeca-tetraene | unidentified compounds |
| Lewatit ® SPC 118 | $CuCl_2$ | 69.1 | 46.8 | 44.3 | 4.0 | 0.1 | 0.0 | 4.1 | 0.1 | 0.7 |
| | $CuBr_2$ | 65.1 | 47.7 | 45.0 | 3.8 | 0.0 | 0.0 | 2.8 | 0.1 | 0.4 |
| | $CuSO_4$ | 55.5 | 32.2 | 31.8 | 13.8 | 2.0 | 1.1 | 1.7 | 1.4 | 16.6 |
| | $Cu(NO_3)_2$ | 55.1 | 39.0 | 35.9 | 13.6 | 1.0 | 0.3 | 1.5 | 0.4 | 8.1 |
| | $Cu(AcO)_2$ | 59.7 | 34.1 | 33.2 | 15.0 | 1.7 | 1.1 | 0.9 | 1.2 | 12.9 |
| Lewatit ® SPC 108 | $CuCl_2$ | 61.5 | 36.8 | 33.8 | 13.8 | 0.7 | 0.1 | 0.9 | 0.0 | 13.9 |
| | $CuBr_2$ | 68.6 | 46.6 | 43.9 | 4.9 | 0.0 | 0.0 | 2.9 | 0.1 | 1.7 |
| Amberlyst ® R 15 | $CuBr_2$ | 63.5 | 37.0 | 35.1 | 14.8 | 0.9 | 0.5 | 1.1 | 1.2 | 9.5 |

Capacity of autoclave: 0.3 L: autogenous pressure, 90° C., 10 h reaction time
Selectivity and conversion based on butadeien Ion exchanger in H⁺ or Cu form rinsed with water and butanol
0.90 mol of butadiene
0.909 mol of butanol
AcO = acetate Example 5

(isomerization of adduct III to adduct II)

A stirred autoclave was filled with 6.0 g of n-butanol, 2.0 g of 3-butoxybutene-1 and 1.2 g of dried Lewatit® SCS 118 ion exchanger in the H⁺ form. The reaction mixture was heated to 105° C. and after 2 and 6 h of reaction time a sample was taken and the ratio of 3-butoxybutene-1 to 1-butoxybutene-2 was determined by gas chromatography. The change of this ratio with reaction time is shown in Table 5.

TABLE 5

| Reaction Time [h] | Molar Ratio of 3-butoxybutene-1 to 1-butoxybutene-2 |
|---|---|
| 0 | 100:0 |
| 2 | 70:30 |
| 6 | 61:39 |

Example 6

Using the apparatus described in Example 3, 1,3-butadiene, n-butanol and a mixture of butoxybutenes as produced when effecting the addition of n-butanol to 1,3-butadiene, from which mixture the major portion of the 1-butoxyene-2 had previously been separated off by distillation, were mixed in the liquid phase upstream of the reactor and then continuously passed through the ion exchanger bed under a pressure of 20 bar and at various temperatures. The results of these tests are listed in table 6. All of the analyses were effected by means of calibrated gas chromatography.

Example 7

(for comparison with Example 6)

Example 7 was carried out in the same manner as Example 6 except that only 1,3-butadiene and n-butanol but no butoxybutenes were fed to the reactor. The results are listed in Table 6.

Comparison of the results of Examples 6 and 7 in Table 6 shows that the measure of recycling the undesirable 3-butoxybutene-1 formed in the addition of n-butanol to 1,3-butadiene to the addition reaction suppresses renewed formation of this by-product.

c) In a manner similar to that described in Example 8b) 0.90 mol of n-butanol and 0.88 mol of 1,3-butadiene were caused to react in the presence of 5 g of the (β-zeolite in the H$^+$ form prepared as described in Example 8a). At a conversion rate of 40.0% 3-butoxybutene-1 was formed at a selectivity of 42.5% and 1-butoxybutene-2 at a selectivity of 16.5%.

Example 9

Addition of n-butanol to 1,3-butadiene in the presence of a homogeneous transition metal element catalyst A stirred autoclave having a capacity of 0.3 L was filled with 74.0 g (1.0 mol) of n-butanol, 0.205 g (0.66 mol) of palladium acetonylacetonate and 2.02 g (7.3 mol) of 1-(diisopropylphosphino)-3-(di-t-butyl-phosphino)propane under a blanket of nitrogen. 34.7 g (0.64 mol) of 1,3-butadiene were then forced in. After a reaction time of 20 h at 80° C. under a pressure of 9 bar, the reaction was stopped and the reaction mixture was analyzed by gas chromatography.

Butadiene conversion: 88%

Selectivity toward the formation of 3-butoxybutene-1:64.5%

Selectivity toward the formation of 1-butoxybutene-2:34.3%.

Example 10

(isomerization of the adduct II to the enol ether IV)

TABLE 6

Continuous addition of n-butanol to butadiene with recycling of 3-butoxybutene-1

| | Feed rate [g/h] | | | | | Conversion | Effluent [g/h] | | | Sum | |
|---|---|---|---|---|---|---|---|---|---|---|---|
| Ex. | Butanol | Butadiene | 3-Butoxy butene-1 | 1-Butoxy butene-2 | Temp [°C.] | of Butadiene [%] | 1-Butoxy butene-1 | Butoxy-butene-2 | Butoxy-octadiene | Oct.[2) VCH[3) | Unidentified compounds |
| 6 | 38.5 | 12.6 | 12.8 | 1.3 | 81 | 44.5 | 15.8 | 10.2 | 0.9 | 0.3 | 0.0 |
| 6 | 38.2 | 11.8 | 12.7 | 1.3 | 91 | 61.3 | 15.1 | 13.6 | 1.2 | 0.3 | 0.6 |
| 7 | 49.6 | 13.7 | — | — | 91 | 79.2 | 11.6 | 11.0 | 1.1 | 0.2 | 0.6 |

Oct.[2) = octatriene
VC[3) = vinylcyclohexene

Example 8

Addition of n-butanol to 1,3-butadiene by zeolite catalysis a) Preparation of the H$^+$ form of the zeolites A commercial Y-type zeolite in the Na form (modulus: 5) was converted to the H$^+$ form as follows:

100 g of the zeolite were treated with ammonium sulfate solution at 80° C. for the purpose of ion exchange, then washed with water, dried at 110° C. and calcined at 500° C. for five hours. This treatment was repeated once. The resulting Y-type zeolite (H$^+$ form) contained 0.02 wt % of sodium and its X-ray diagram corresponded to the typical X-ray diffraction pattern of a Y-type zeolite in the H$^+$ form (FAU structure).

An Na-β-zeolite prepared in accordance with Example 1 of U.S. Pat. No. 4,891,458 was treated in the same manner.

b) A stirred autoclave having a capacity of 0.3 L was filled with 67.0 g (0.90 mol) of n-butanol and 5 g of the Y-type zeolite in the H$^+$ form prepared as described in Example 8a). 49.7 g (0.92 mol) of 1,3-butadiene were then forced in. After a reaction time of 6 h at 130° C. under a pressure of 9 bar there was found, at a 1,3-butadien conversion of 35.9%, a selectivity toward the formation of 3-butoxybutene-1 of 32.4% and a selectivity toward the formation of 1-butoxybutene-2 of 20.3%.

Under a blanket of argon, 40 g (312 mmol) of 1-butoxybutene-2 in a melt of 100 g (382 mmol) of triphenylphosphine (PPh$_3$) and 5 g (5.4 mmol) of HRh(PPh$_3$)$_3$CO were caused to react for 200 min at 120° C. with stirring. The products were then taken up in toluene and analyzed by gas chromatography. The conversion to 1-butoxybutene-2 was 48.5%, the selectivity toward the formation of 1-butoxybutene-1was 95.5% and the selectivity toward the formation of 1-butoxybut-3-ene was 4.5%.

Example 11

Example 10 was repeated except that an equimolar CO/H$_2$ mixture was used instead of argon. After 240 min of reaction time the products were taken up in toluene and analyzed by gas chromatography. The conversion to 1-butoxyene-1 was 50.3%, the selectivity toward the formation of 1-butoxybutene-1 was 99.5% and the selectivity toward the formation of 1-butoxybutene-3 was 0.5%.

Example 12

(isomerization of the adduct II to the enol ether IV and hydrolysis of the enol ether IV to n-butyraldehyde in a single stage using a homogeneous catalyst)

A mixture of 2.0 g of 1-butoxybutene-2, 3.0 g of water and 0.20 g of the catalyst HRuCl(CO)(PPh$_3$)$_3$ was caused to react in a stirred autoclave at 160° C. under autogenous pressure over a period of 7 h. At a conversion rate of 69.3%, the selectivity toward the formation of n-butyraldehyde was 85.6%. 1-butanol was produced from 1-butoxyene-2 at a selectivity of 96.1%.

Example 13

Example 12 was repeated with the addition of 2.0 g of the solvent diethylene glycol dimethyl ether. At a conversion rate of 78.3%, n-butyraldehyde was formed at a selectivity of 86.5%.

Example 14

(isomerization of the adduct II to the enol ether IV and hydrolysis/hydrogenation of the enol ether IV to n-butanol in a single stage using a homogeneous catalyst)

Hydrogen was introduced into a mixture of 3.0 g of water, 0.022 g of the catalyst HRuCl(CO)(PPh$_3$)$_3$, 0.028 g of triphenylphosphine, and 2.02 g of 1-butoxybutene-2 at 120° C. and under a pressure of 12 bar with stirring until no further water uptake could be observed. After 3 h of reaction time the reaction mixture was analyzed by means of calibrated gas chromatography. At a conversion rate of 99%, n-butanol was formed at a selectivity of 97.7%.

Example 15

(isomerization of the adduct II to the enol ether IV and hydrogenation of the enol ether to n-butanol in a single stage using a heterogeneous catalyst in the gaseous phase)

200 mL of a copper on activated charcoal catalyst, which had a copper content, calculated as CuO, of 10 wt %, were placed in a reactor and the catalyst was activated over a period of one hour in a stream of hydrogen at atmospheric pressure and at a temperature rising from initially 150° C. to an end temperature of 260° C.

The reactor was then cooled to 210° C. and 32.0 g/h of water and 9.4 g/h 1-butoxyene-2 were passed, at atmospheric pressure, through the reactor via a preheater heated at 200° C. At the same time, a stream of hydrogen was fed to the reactor at a rate of 15 L/h. After cooling, the two-phase liquid effluent was analyzed by means of calibrated gas chromatography. At a conversion rate of 94%, n-butanol was formed at a selectivity of 95.8%. The selectivity toward butyraldehyde was 4.2%.

We claim:

1. A process for the preparation of n-butyraldehyde and/or n-butanol, wherein
   a) 1,3-butadiene or 1,3-butadiene containing hydrocarbon streams are caused to react with an alcohol of the formula

ROH      I, in which the radical R is a C$_2$–C$_{20}$ alkyl or alkenyl group which may be unsubstituted or substituted by 1 or 2 C$_1$–C$_{10}$ alkoxy or hydroxy groups, or R is a C$_6$–C$_{10}$-aryl group or a C$_7$–C$_{11}$-aralkyl group or the methyl group, at elevated temperature and under superatmospheric pressure in the presence of a Brönsted acid or in the presence of a complex of a Group Ib), VIIb), or VIIIb) element with ligands containing phosphorus or nitrogen to form a mixture of the adducts of the formulas II

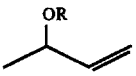

and III

b) the adduct III is isomerized to the adduct II,
c) the adduct II is isomerized in the presence of a homogeneous or heterogeneous transition metal element catalyst in the liquid phase or in the presence of a heterogeneous catalyst containing a transition metal element in the gaseous phase to form the enol ether of the formula IV

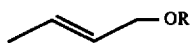

and d) n-butyraldehyde and/or n-butanol is/are produced from this ether IV by the reaction thereof with hydrogen and water or water only in the presence of a homogeneous or heterogeneous transition metal element catalyst in the liquid phase or in the presence of a transition metal element containing heterogeneous catalyst in the gaseous phase and the alcohol ROH I is again liberated, and the liberated alcohol ROH I is recycled to the stage defined as partial reaction a).

2. A process as defined in claim 1, wherein the reaction of 1,3-butadiene with an alcohol ROH I is carried out in the presence of an acid ion exchanger.

3. A process as defined in claim 1, wherein the reaction of 1,3-butadiene with an alcohol ROH I is carried out in the presence of an acid ion exchanger, which is additionally doped with at least one Lewis acid.

4. A process as defined in claim 1, wherein the reaction of 1,3-butadiene with an alcohol ROH I is carried out in the presence of a zeolite in the H$^+$ form, a bleaching earth, or an acid aluminum phosphate.

5. A process as defined in claim 1, wherein the reaction of 1,3-butadiene with an alcohol ROH I is carried out in the presence of a catalyst comprising an alkyl, aryl, or aryl-alkyl phosphine complex of a Group Ib), VIIb), or VIIIb) transition metal.

6. A process as defined in claim 1, wherein the reaction of 1,3-butadiene with an alcohol ROH I is carried out in the presence of a catalyst comprising an alkyl, aryl, or aryl-alkyl phosphine complex of rhodium, ruthenium, nickel, palladium, iridium, or platinum.

7. A process as defined in claim 1, wherein the isomerization of the adduct III to the adduct II is carried out in the presence of a catalyst such as is used for the catalysis of the addition of the alcohol ROH I to 1,3-butadiene defined as partial reaction a).

8. A process as defined in claim 1, wherein the adduct III is separated from the adduct II and the adduct III is then recycled to the partial reaction a) and is isomerized therein to the adduct II.

9. A process as defined in claim 1, wherein the partial reactions c)—isomerization of the adduct II to the enol ether IV and d)—hydrolysis or combined hydrolysis/hydrogenation of the enol ether IV to n-butyraldehyde and n-butanol—are carried out in a single process stage.

10. A process as defined in claim 1, wherein the partial reactions c) and d) are carried out in a single process stage in the liquid phase in the presence or absence of an added solvent.

11. A process as defined in claim 1, wherein the partial reactions c) and d) are carried out in a single process stage in the liquid phase in the presence of an added solvent, which is an alcohol.

12. A process as defined in claim 1, wherein the partial reactions c) and d) are carried out in a single process stage in the liquid phase in the presence of an added solvent, which is n-butanol.

13. A process as defined in claim 1, wherein the partial reactions c) and d) are carried out in a single process stage in the liquid phase in the presence of a homogeneous catalyst soluble in the reaction medium in the presence or absence of an added solvent.

14. A process as defined in claim 1, wherein the partial reactions c) and d) are carried out in a single process stage in the liquid phase in the presence of a homogeneous catalyst soluble in the reaction medium, which catalyst is a mono- or poly-dentate phosphine or phosphite complex of a Group Ib), VIb), VIIb), and VIIIb) element and in the presence or absence of an added solvent.

15. A process as defined in claim 1, wherein the partial reactions c) and d) are carried out in a single process stage in the liquid phase in the presence of a homogeneous catalyst soluble in the reaction medium and comprising a phosphine or phosphite complex of a Group Ib), VIb), VIIb), and VIIIb) element and in the presence of hydrogen and water and excess phosphine or phosphite ligands, and in the presence or absence of an added solvent to produce n-butanol.

16. A process as defined in claim 1, wherein the partial reactions c) and d) are carried out in a single process stage in the liquid phase in the presence of a homogeneous catalyst soluble in the reaction medium, which catalyst is a complex of a nitrogenous chelate ligand with a Group Ib), VIb), VIIb), or VIIIb) element and in the presence or absence of an added solvent.

17. A process as defined in claim 1, wherein the partial reactions c) and d) are carried out in a single process stage in the liquid phase in the presence of a homogeneous catalyst soluble in the reaction medium, which catalyst is a chelate complex of a bipyridine or phenanthroline ligand with a Group Ib), VIb), VIIb), and VIIIb) element and in the presence or absence of an added solvent.

18. A process as defined in claim 1, wherein the partial reactions c) and d) are carried out in a single process stage in the liquid phase in the presence of a homogeneous catalyst soluble in the reaction medium, which catalyst is a salt of a Group Ib), VIb), VIIb), and VIIIb) element and in the presence or absence of an added solvent.

19. A process as defined in claim 1, wherein the partial reactions c) and d) are carried out in a single process stage in the liquid phase in the presence of a homogeneous catalyst soluble in the reaction medium, which catalyst is an aquo, ammine, halo, cyano, carbonyl, amino, or acetylacetonate complex of a Group Ib), VIb), VIIb), or VIIIb) element and in the presence or absence of an added solvent.

20. A process as defined in claim 1, wherein the partial reactions c) and d) are carried out in a single process stage in the liquid phase in the presence of a homogeneous catalyst soluble in the reaction medium, which catalyst is a salt or an aquo, ammine, halo, cyano, amino, or acetylacetonate complex of a Group Ib), VIb), VIIb), and VIIIb) element, in the presence of water and in the presence or absence of an added solvent, to produce n-butyraldehyde.

21. A process as defined in claim 1, wherein the partial reactions c) and d) are carried out in a single process stage in the liquid phase in the presence of an organotrioxorhenium compound of the formula V

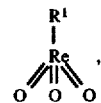

in which $R^1$ is a $C_1$–$C_{20}$ alkyl group, an unsubstituted cyclopentadienyl group or a cyclopentadienyl group substituted by from 1 to 5 $C_1$–$C_4$ alkyl groups, a $C_6$–$C_{10}$ aryl group or a $C_7$–$C_{11}$-aralkyl group, in the presence of water and in the presence or absence of an added solvent, to produce n-butyraldehyde.

22. A process as defined in claim 1, wherein the partial reactions c) and d) are carried out in a single process stage in the liquid phase in the presence of a homogeneous catalyst soluble in the reaction medium, which catalyst is an alkali metal, alkaline earth metal or onium salt of an oxy-acid of vanadium or rhenium, or in the presence of dirhenium heptoxide and in the presence of water and in the presence or absence of an added solvent, to produce n-butyraldehyde.

23. A process as defined in claim 1, wherein the partial reactions c) and d) are carried out in a single process stage in the liquid phase in the presence of a homogeneous catalyst soluble in the reaction medium and in the presence of hydrogen and water or water and in the presence or absence of an added solvent, and the catalyst solution obtained following the separation of the products n-butyraldehyde and n-butanol is re-used for carrying out the partial reactions c) and d).

24. A process as defined in claim 1, wherein the partial reactions c) and d) are carried out in the liquid phase in a single process stage in the presence of at least one heterogeneous catalyst substantially insoluble in the reaction medium in the presence or absence of a solvent.

25. A process as defined in claim 1, wherein the partial reactions c) and d) are carried out in the liquid phase in a single process stage in the presence of at least one heterogeneous catalyst containing one or more Group Ib), VIb), VIIb), and VIIIb) elements in the presence or absence of one or more Group Vb) elements in the presence or absence of a solvent.

26. A process as defined in claim 1, wherein the partial reactions c) and d) are carried out in the liquid phase in a single process stage in the presence of at least one heterogeneous catalyst containing one or more Group Ib), VIb), VIIb), and VIIIb) elements in the presence or absence of one or more Group Vb) elements and also containing a support material and in the presence or absence of a solvent.

27. A process as defined in claim 1, wherein the partial reactions c) and d) are carried out in the liquid phase in a single process stage in the presence of at least one heterogeneous catalyst containing one or more Group Ib), VIb), VIIb), and VIIIb) elements in the presence or absence of one or more Group Vb) elements and additionally containing aluminum oxide, titanium dioxide, silicon dioxide, zirconium dioxide, a silicate, an argillaceous earth, a zeolite and/or activated charcoal as support material and in the presence or absence of a solvent.

28. A process as defined in claim 1, wherein the partial reactions c) and d) are carried out in the liquid phase in a single process stage in the presence of at least one heterogeneous catalyst containing copper and in the presence or absence of a solvent.

29. A process as defined in claim 1, wherein the partial reactions c) and d) are carried out in the liquid phase in a single process stage in the presence of at least one heterogeneous catalyst, which catalyst is disposed in a fixed bed and in the presence or absence of a solvent.

30. A process as defined in claim 1, wherein the partial reactions c) and d) are carried out in the liquid phase in a single process stage in the presence of at least one heterogeneous catalyst, which catalyst is disposed in 2 to 5 fixed beds and in the presence or absence of a solvent.

31. A process as defined in claim 1, wherein the partial reactions c) and d) are carried out in the gaseous phase in a single process stage in the presence of at least one heterogeneous catalyst.

32. A process as defined in claim 1, wherein the partial reactions c) and d) are carried put in the gaseous phase in a single process stage in the presence of at least one heterogeneous catalyst containing one or more Group Ib, VIb), VIIb), and VIIIb) elements in the presence or absence of one or more Group Vb) elements.

33. A process as defined in claim 1, wherein the partial reactions c) and d) are carried out in the gaseous phase in a single process stage in the presence of at least one heterogeneous catalyst containing one or more Group Ib), VIb), VIIb), and VIIIb elements in the presence or absence of one or more Group Vb) elements and additionally containing a support material.

34. A process as defined in claim 1, wherein the partial reactions c) and d) are carried out in the gaseous phase in a single process stags in the presence of at least one heterogeneous catalyst containing one or more Group Ib), VIb), VIIb), and VIIIb) elements in the presence or absence of one or more Group Vb) elements and additionally containing aluminum oxide, titanium dioxide, zirconium dioxide, silicon dioxide, a silicate, an argillaceous earth, a zeolite and/or activated charcoal as support material.

35. A process as defined in claim 1, wherein the partial reactions c) and d) are carried out in the gaseous phase in a single process stage in the presence of at least one heterogeneous catalyst, which contains a Group Ib, VIb), VIIb), and VIIIb) element in the presence or absence of one or more Group Vb) elements and is disposed in at least one fixed bed or a fluidized bed.

36. A process as defined in claim 1, wherein,the partial reactions c) and d) are carried out in the gaseous phase in a single process stage in the presence of at least two catalysts, which contain one or more Group Ib), VIb), VIIb), and VIIIb) elements in the presence or absence of one or more Group Vb) elements and are in the form of a mixture disposed in at least one fixed bed.

37. A process as defined in claim 1, wherein the partial reactions c) and d) are carried out in the gaseous phase in a single process stage in the presence of a heterogeneous catalyst or a number of heterogeneous catalysts, which contain one or more Group Ib), VIb), VIIb), and VIIIb) elements in the presence or absence of one or more Group Vb) elements and which are disposed in at least 2 fixed beds.

38. A process as defined in claim 1, wherein the partial reactions c) and d) are carried out in the liquid phase and in the gaseous phase in successive process stages.

39. A process as defined in claim 1, wherein the partial reactions c) and d) are carried out in the liquid phase in successive process stages using homogeneous and heterogeneous catalysts in the individual process stages.

40. A process as defined in claim 1, wherein the partial reactions c) and d) are carried out in successive process stages in the liquid phase and in the gaseous phase using homogeneous and heterogeneous catalysts.

41. A process as defined in claim 1, wherein the alcohol ROH used is n-butanol.

* * * * *

UNITED STATES PATENT AND TRADEMARK OFFICE
CERTIFICATE OF CORRECTION

PATENT NO.: 5,705,707

DATED: January 6, 1998

INVENTOR(S): KANAND et al.

It is certified that error appears in the above-identified patent and that said Letters Patent is hereby corrected as shown below:

Column 39, claim 32, line 11, "put" should be --out--.

Column 39, claim 34, line 25, "stags" should be --stage--.

Column 40, claim 36, line 5, "wherein, the" should be --wherein the--.

Signed and Sealed this

Third Day of March, 1998

BRUCE LEHMAN

*Attest:*

*Attesting Officer*     Commissioner of Patents and Trademarks